(12) United States Patent
Sappok et al.

(10) Patent No.: US 10,168,358 B2
(45) Date of Patent: Jan. 1, 2019

(54) ADVANCED RADIO FREQUENCY SENSING PROBE

(71) Applicant: Filter Sensing Technologies, Inc., Malden, MA (US)

(72) Inventors: Alexander Sappok, Cambridge, MA (US); Roland Smith, III, Medford, MA (US); Leslie Bromberg, Sharon, MA (US)

(73) Assignee: CTS CORPORATION, Lisle, IL (US)

( * ) Notice: Subject to any disclaimer, the term of this patent is extended or adjusted under 35 U.S.C. 154(b) by 625 days.

(21) Appl. No.: 14/535,398

(22) Filed: Nov. 7, 2014

(65) Prior Publication Data

US 2015/0123688 A1    May 7, 2015

Related U.S. Application Data

(60) Provisional application No. 61/901,052, filed on Nov. 7, 2013.

(51) Int. Cl.
    *G01R 1/067* (2006.01)
    *G01N 22/00* (2006.01)

(52) U.S. Cl.
    CPC ......... *G01R 1/06772* (2013.01); *G01N 22/00* (2013.01)

(58) Field of Classification Search
    CPC ............ G01R 31/2656; G01R 31/2822; G01R 31/3025; G01R 31/311
    See application file for complete search history.

(56) References Cited

U.S. PATENT DOCUMENTS

| | | | |
|---|---|---|---|
| 3,701,086 A | 10/1972 | Sherman et al. | |
| 4,204,549 A | 5/1980 | Paglione | |
| 4,477,771 A | 10/1984 | Nagy et al. | |
| 4,841,988 A | 6/1989 | Fetter et al. | |
| 4,945,318 A | 7/1990 | Kabachinski et al. | |
| 5,539,851 A * | 7/1996 | Taylor | H01B 11/1891 174/102 R |
| 6,123,567 A * | 9/2000 | McCarthy | H01R 4/5033 439/427 |

(Continued)

FOREIGN PATENT DOCUMENTS

| CN | 202759006 U | 2/2013 |
|---|---|---|
| WO | 9200766 A1 | 1/1992 |
| WO | 2009008525 A1 | 1/2009 |

OTHER PUBLICATIONS

International Search Report and Written Opinion dated Feb. 12, 2015 in corresponding PCT application No. PCT/US14/064475.

(Continued)

*Primary Examiner* — Tung X Nguyen
(74) *Attorney, Agent, or Firm* — Daniel Deneufbourg

(57) ABSTRACT

A radio-frequency probe system with a transmitting or receiving element integrated into a cable assembly is disclosed. In some embodiments a preferred configuration may contain one or more sensing elements integrated into the transmitting or receiving element. In another embodiment, the radio frequency probe comprises an antenna body fixed to a coaxial cable, in which the center conductor of the coaxial cable serves as the transmitting or receiving element. A method for monitoring, transmitting, or detecting one or more parameters using a single radio frequency probe is also disclosed.

5 Claims, 16 Drawing Sheets

(56) References Cited

U.S. PATENT DOCUMENTS

| | | | |
|---|---|---|---|
| 6,596,393 B1 * | 7/2003 | Houston | C23F 11/149 |
| | | | 174/109 |
| 7,194,383 B2 | 3/2007 | Clarke et al. | |
| 8,384,396 B2 | 2/2013 | Bromberg et al. | |
| 2008/0224922 A1 | 9/2008 | Cleland et al. | |
| 2011/0025581 A1 | 2/2011 | Geer et al. | |

OTHER PUBLICATIONS

M Feulner et al: 11 Microwave-Based Diesel Particulate Filter Monitoring—Soot Load Determination and Influencing Parameters, May 16, 2013 (May 16, 2013), DOI: 10.5162/sensor2013/P4.1 Retrieved from the Internet: URL:https://www.ama-science.org/proceedings/details/1605.

John Hansson et al: 11A Method for Estimating Soot Load in a DPF Using an RF-based Sensor Examensarbete utfort i Fordonssystem vid Tekniska hogskolan vid Linkopings universitet av, Jun. 11, 2012 (Jun. 11, 2012), XP055386001, Retrieved from the Internet: URL:https://pdfs.semanticscholar.org/269d/bbc993edlf80c7b86b368d6cflf580a381fl.pdf.

* cited by examiner

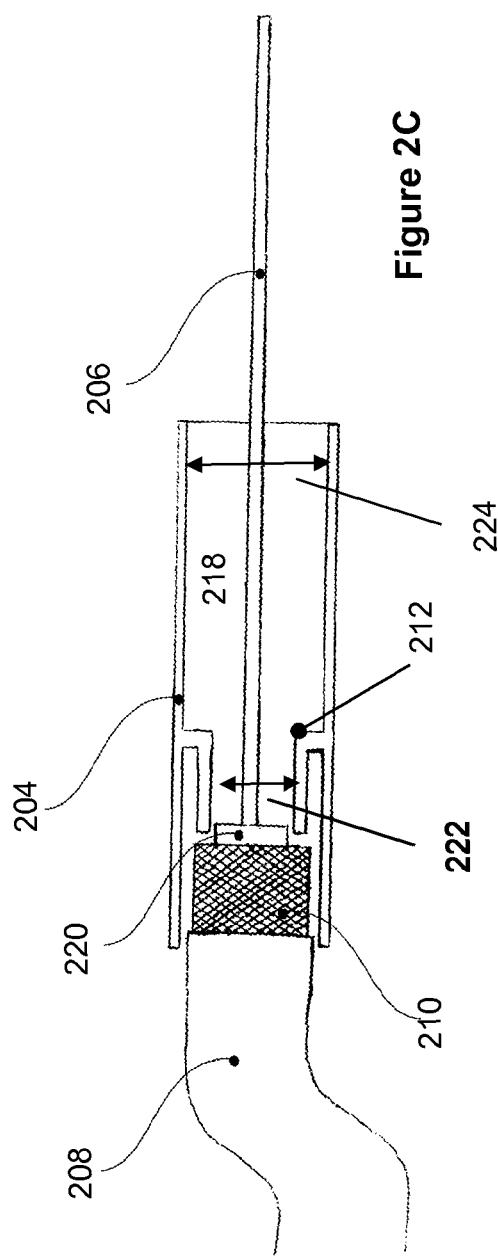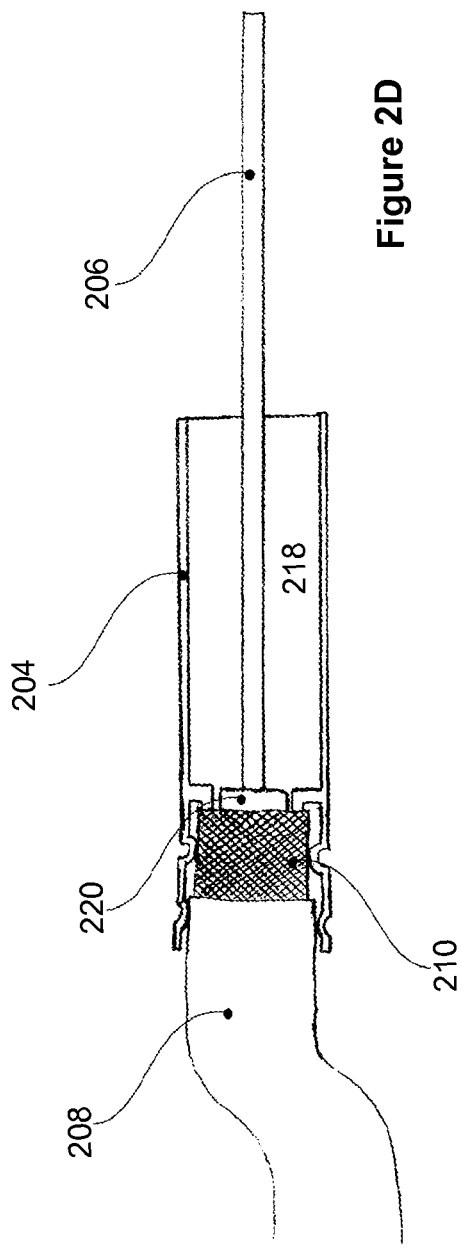

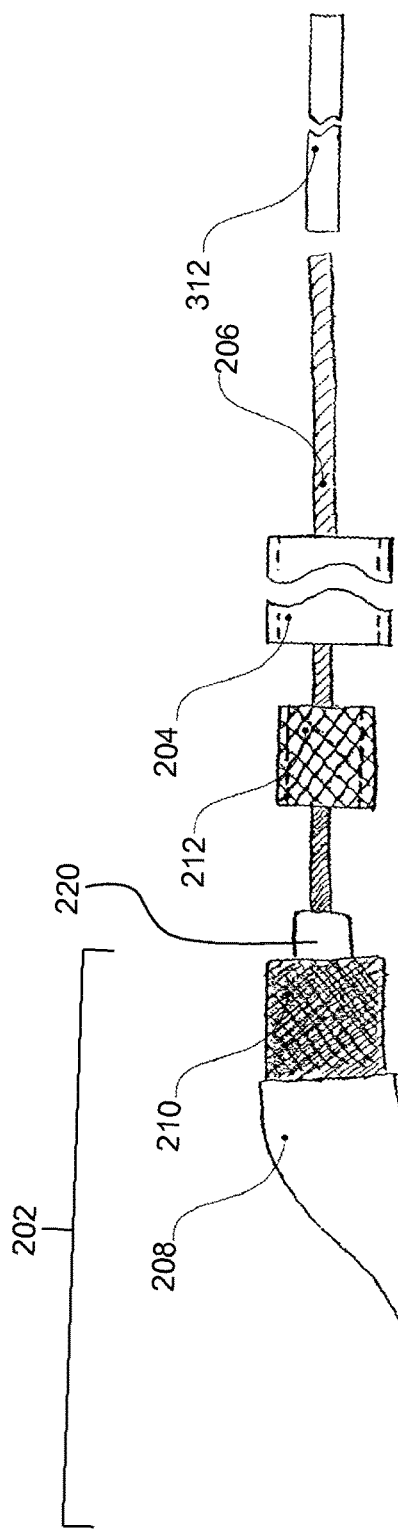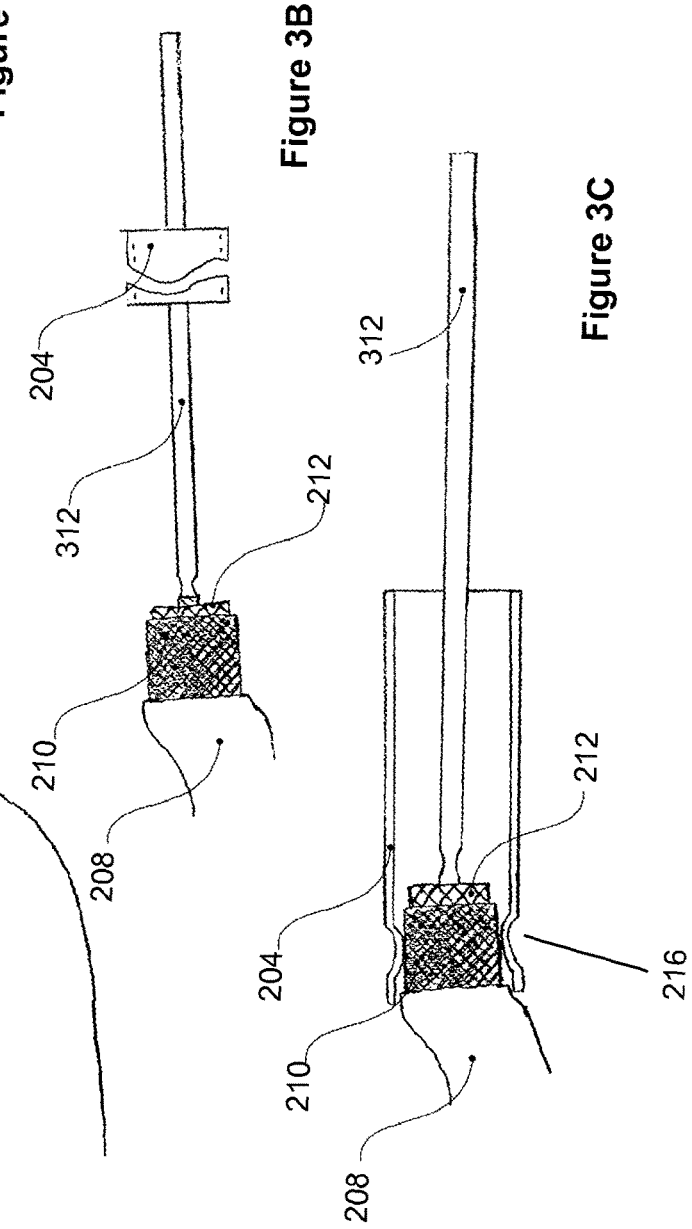

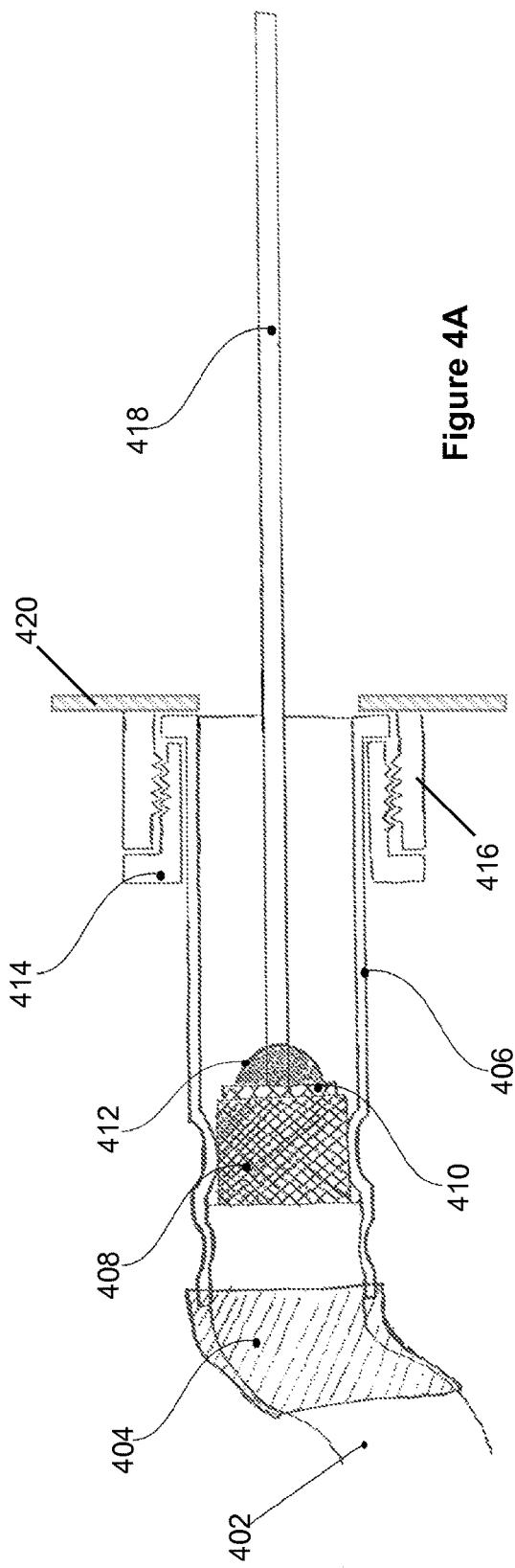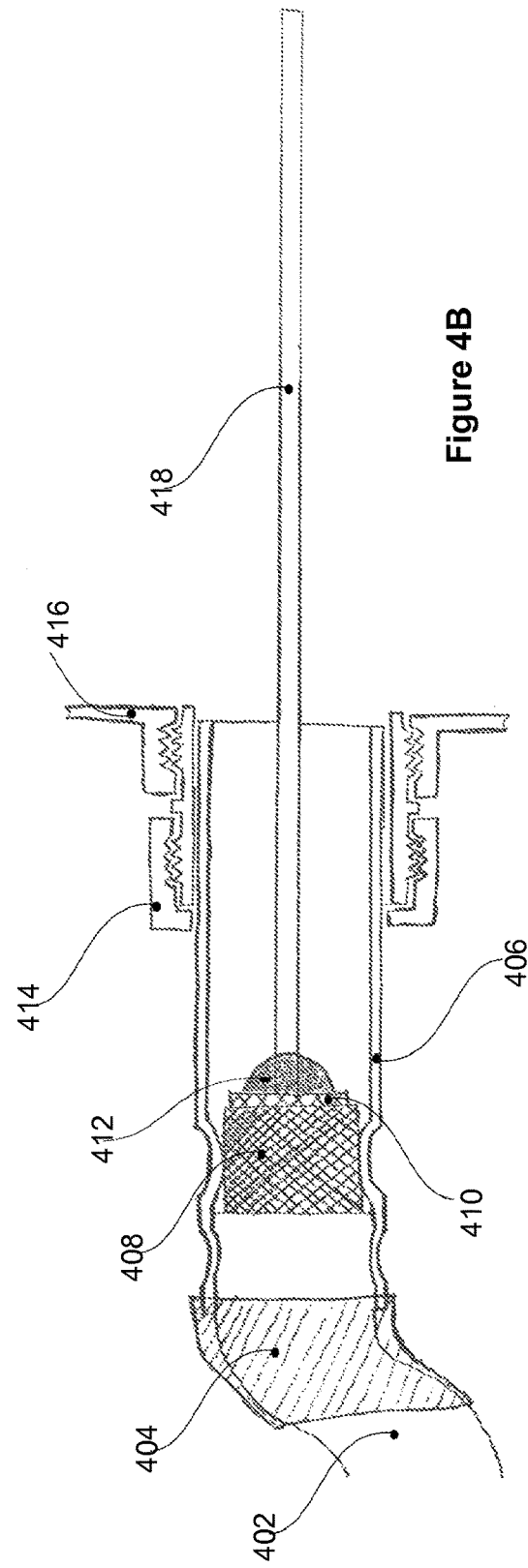

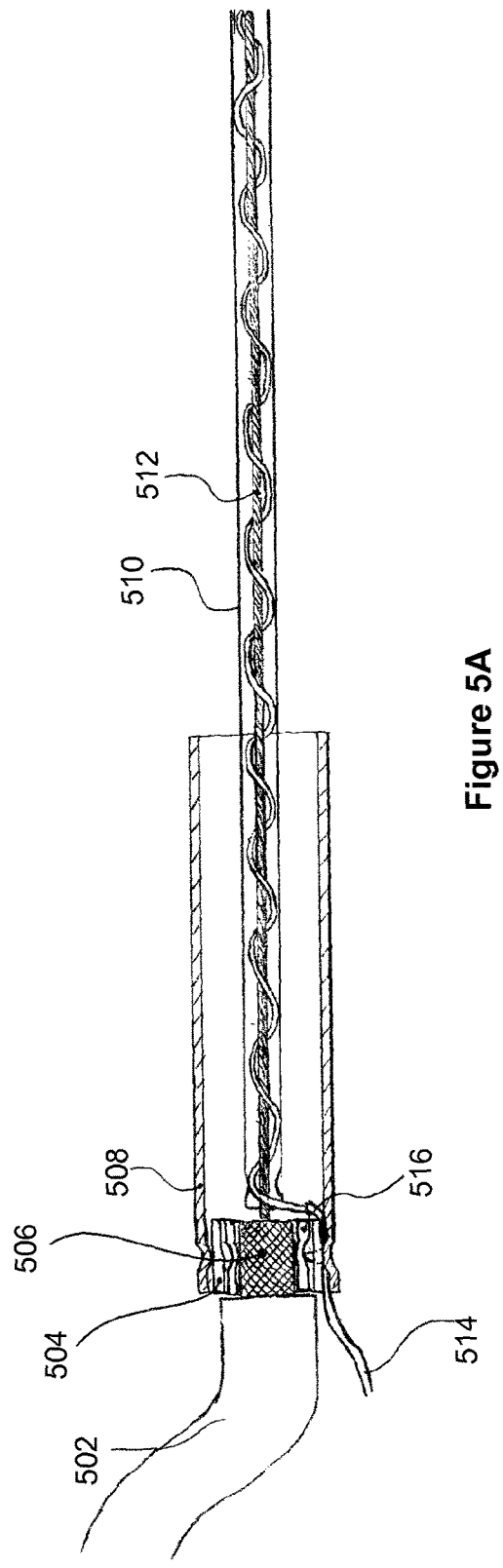
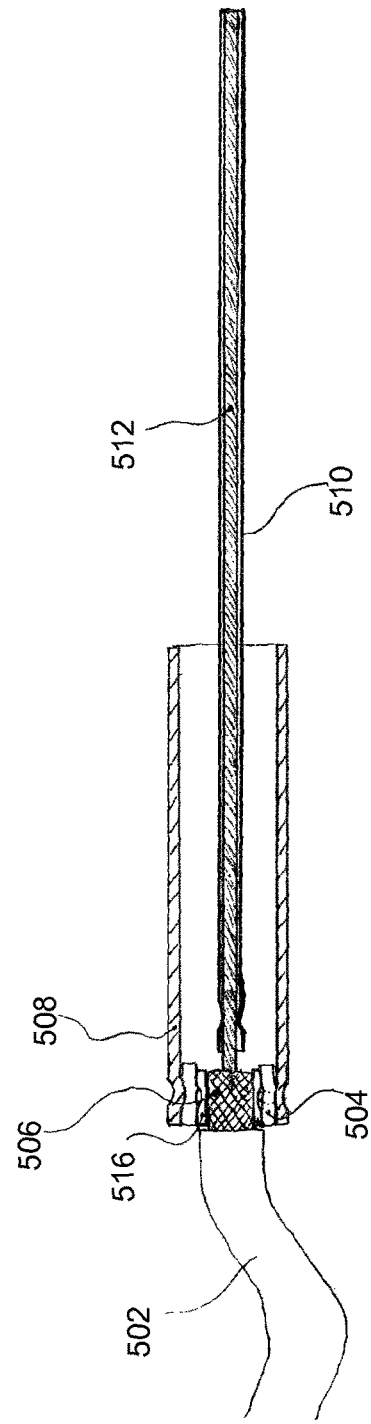
Figure 5A
Figure 5B

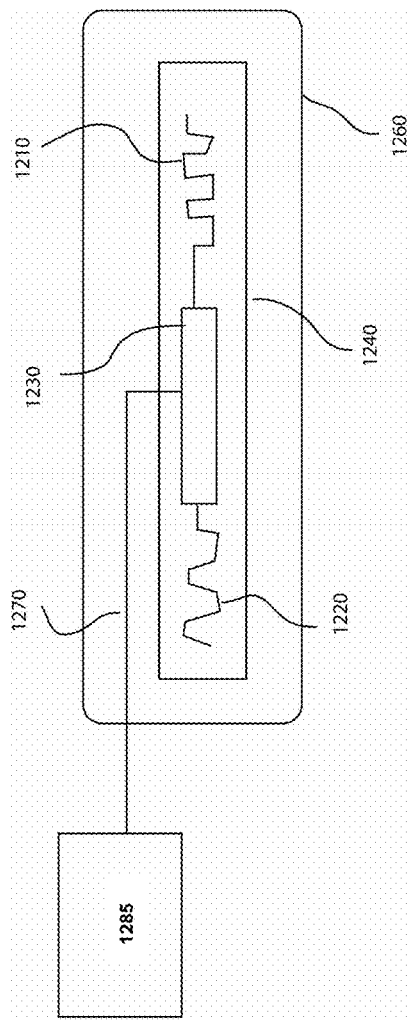
Fig. 12A Antenna assembly where the antennae and the RF electronics are placed on a board.
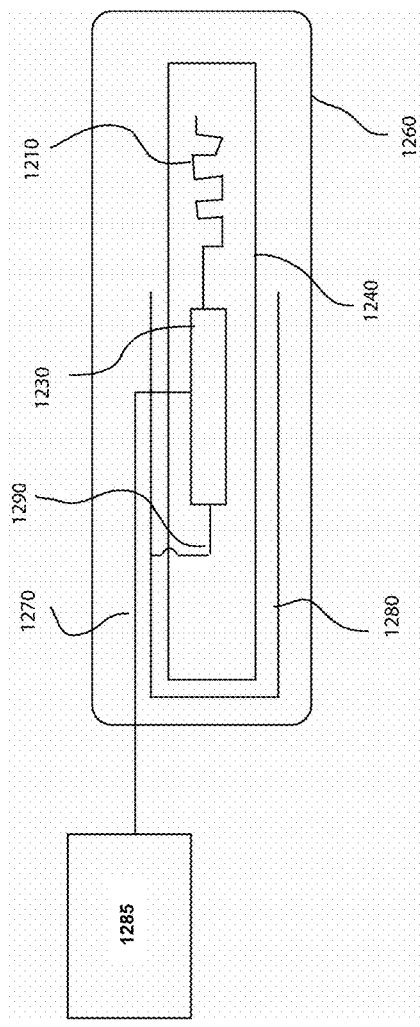
Fig 12B. Alternative antenna assembly where a hollow tube is used as second element of the antenna.

ADVANCED RADIO FREQUENCY SENSING PROBE

This application claims priority of U.S. Provisional Patent Application Ser. No. 61/901,052, filed Nov. 7, 2013, the disclosure of which is incorporated by reference in its entirety.

This invention was made with U.S. Government support under Contract Number DE-EE0005653 awarded by the United States Department of Energy. The Government has certain rights in this invention.

BACKGROUND

Radio frequency (RF)—and microwave-based sensing techniques, including cavity perturbation methods and the like, are used in many applications ranging from laboratory and research instrumentation to process control systems and even on-vehicle sensors. In many applications, antennas or probes are used to transmit and/or receive radio frequency or microwave signals to conduct these measurements. Oftentimes, additional information is required to accurately interpret the measurement results, as external factors, such as temperature or moisture for example, may introduce additional variables that influence the measurements.

There is a further need in many applications for robust sensing systems, capable of withstanding high levels of vibrations, large temperature variations, harsh or corrosive environments, exposure to the elements, and similar demanding requirements. Many of these requirements can only be met through complex, cumbersome, and expensive systems, which suffer from the following limitations.

First, current sensing systems employing antennas or probes to transmit and receive radio frequency or microwave signals require additional sensors to measure multiple parameters. Temperature sensors, moisture sensors, pressure sensors, and the like are often required (in addition to the antenna or probe) to conduct these ancillary measurements, adding additional cost and complexity to the system.

Second, many conventional antennas and RF/microwave probes are not robust and are incapable of surviving extended operation with exposure to high temperatures, high vibration levels, thermal shock, corrosive or dirty environments, oxidizing or reducing conditions, and the like. Environmental exposure, rain, snow, and salt water for example, as well as exposure to chemicals and solvents, such as oils, fuels, acids, and similar chemicals, is also detrimental to many conventional RF/microwave probes and antennas.

Third, RF/microwave probes and antennas designed for operation in harsh environments are generally expensive, large and bulky, and ill-suited for use in low-cost measurement systems. The expense in these systems stems from both the requirement to utilize more exotic and higher priced materials, as well as the added cost and complexity involved in the manufacture and assembly of the antenna or probe and associated connectors.

Fourth, conventional antenna systems suffer from limitations of variability introduced by reflections, losses, and incorrect impedance matching. Many of these sources of variability are related to the antenna design itself and the manner in which the antenna is connected to the signal cable. For example, most antennas require additional components to connect the antenna to the signal cable, such as interconnects and ancillary components. Not only do these components exhibit some inherent variability, which may also vary over time (corrosion, loosening, moisture induction, etc.), but they are also subject to operator error, including misalignment, over-tightening, under-tightening, reliability and the like.

Fifth, radio frequency connectors suitable for use in the microwave range are expensive, particularly when high temperature operation is required. Robust connectors, such as Type N for example, are also bulky, making them ill-suited for applications where a small form-factor is required. In some cases, the size of these connectors may be of the same order as the actual component or sensor.

Sixth, the use of an interconnect on the end of an RF probe or antenna, such as a conventional RF connector (BNC, SMA, Type N, and many others) allows for the connection of any type of cable to the antenna with the same type of matching connector, or with a different type of connectors through the use of a suitable adapter. In applications where the measurement, or operation of the system, requires the use of a cable with specific characteristics (impedance, length, temperature rating, or similar performance specifications), additional sources of error may easily be introduced when the connecting cable is replaced with another cable not meeting the required specifications. Thus, measurement systems in which the antennas and RF probes contain an interconnect, may be susceptible to errors introduced by the installation of incorrect cables.

Therefore, it would be beneficial if there were an RF probe or antenna system that addressed the problems described above. Such a system would be advantageous in that inherent variability in the probe or antenna performance would be reduced, and sources of operator error eliminated, ultimately improving the performance of the overall measurement system with which the antennas or probes are used. In addition, probes or antennas containing multiple sensing elements, or the ability to monitor multiple parameters, an RF signal and temperature, for example, or an RF signal and pressure in another example or an RF signal and gas or liquid composition in yet another example, would greatly simplify the measurement system, by allowing one or more parameters to be monitored with the same probe.

The probes and antennas described herein may be used in a number of applications, ranging from cavities to transmission lines, and even in free space. One range of applications include systems which monitor changes in the dielectric properties of a material or a mixture of materials in order to deduce some information regarding the state of the system. A particular example of such a system is a moisture measurement system used to monitor moisture levels in various materials. Another example includes fluid blend sensors, where the blend may be composed of one or more liquid, gas, or solid materials, and where changes in the dielectric properties of the mixture of materials may provide some information on the state of the system, such as the composition of the mixture, flow rate, or other parameters of interest.

Yet another example includes a class of radio-frequency measurement systems applied to monitor exhaust emissions or the state of various emission control devices. Radio-frequency or microwave systems used to monitor the loading state of particulate filters, such as the amount of soot or ash accumulated in a diesel particulate filter, is one exemplary application. Another application includes the monitoring of various gaseous species, such as oxygen or oxides of nitrogen (among others), adsorbed onto various catalytic emission aftertreatment components, such as three-way catalytic converters, selective catalytic reduction systems, oxidation catalysts, or lean NOx traps, to name a few. In yet another embodiment, the monitored parameter may be a change in the dielectric properties of the material itself, such as the filter material in the case of a diesel particulate filter, in one example and the catalysts substrate, washcoat, or catalyst material in yet another example. Although aftertreatment filters and catalysts are described and are particularly challenging, any filter system or catalyst system can use the technology described herein.

In many applications, there is a need for antennas or measurement probes suitable for extended operation over a range of conditions, including exposure to high temperatures, vibration, mechanical stresses, water and other liquids, and the like. In addition, such antennas or probes may require periodic removal for inspection, maintenance, or replacement. An antenna or probe system which is robust and exhibits little inherent variability is required to ensure proper operation of these systems, and also minimize errors introduced by operators when installing or replacing such antennas or probes.

Furthermore, many measurement systems suffer from variability introduced by changes in parameters other than the measurement parameter of interest. For example, external variables including moisture, flow, temperature, pressure, composition, or the introduction of contaminants, and the like may also affect the performance of radio-frequency or microwave measurement systems. A particular example is the determination of soot accumulation on particulate filters, in which case the dielectric properties of the soot also vary with temperature. Another example is the dielectric state of the catalyst material or the gas-phase species absorbed or adsorbed on a catalyst, or the liquid or solid phase species collected on a filter. Many other measurement systems exhibit similar cross-sensitivities to temperature and other parameters. It is, thus, desirable to monitor the various parameters that may affect the measurement using a single probe, as opposed to using one or more sensors, where each sensor only measures one specific parameter.

The antenna probe system described herein may be applied to any number of applications in which reducing the variability of the antenna is important to improve the signal. Other applications include those in which the number of additional sensing elements may be reduced through the use of a single antenna probe containing one or more sensing elements.

SUMMARY

This disclosure relates to an advanced radio-frequency probe system with a transmitting or receiving element integrated into a cable assembly. In some embodiments, a configuration may contain one or more sensing elements integrated into the transmitting or receiving element. In another embodiment, the radio frequency probe comprises an antenna body fixed to a coaxial cable, in which the center conductor of the coaxial cable serves as the transmitting or receiving element. A method for monitoring, transmitting, or detecting one or more parameters using a single radio frequency probe is also disclosed. Another embodiment includes electronics for generating the signal inside the antenna assembly, or mounted directly on the antenna assembly eliminating the need for high frequency connectors or cables between the antenna assembly and the RF generator or RF detector.

BRIEF DESCRIPTION OF THE DRAWINGS

FIG. 2C is a cross-sectional view of a preliminary step in the assembly of a coaxial cable with integrated antenna and one piece outer sleeve.
FIG. 2D is a cross-sectional view of a subsequent step in the assembly of a coaxial cable with integrated antenna and one piece outer sleeve.
FIG. 3A shows an initial step in terminating a conventional coaxial cable with an antenna probe.
FIG. 3B shows a second step in terminating a conventional coaxial cable with an antenna probe.
FIG. 3C shows a completed coaxial cable terminated with an antenna probe.
FIG. 4A is a cross-sectional view of an antenna integrated with a coaxial cable showing additional details of the system, including one type of connection.
FIG. 4B is a cross-sectional view of an antenna integrated with a coaxial cable showing additional details of the system, including another type of connection.
FIG. 5A is a radio frequency probe with an integrated second sensing element.
FIG. 5B is a radio frequency probe with a single sensing element.
FIG. 12A is an antenna assembly where the antennae and the RF electronics are placed on a board.
FIG. 12B is an alternative antenna assembly where a hollow tube is used as second element of the antenna.

DETAILED DESCRIPTION

Figure 1:
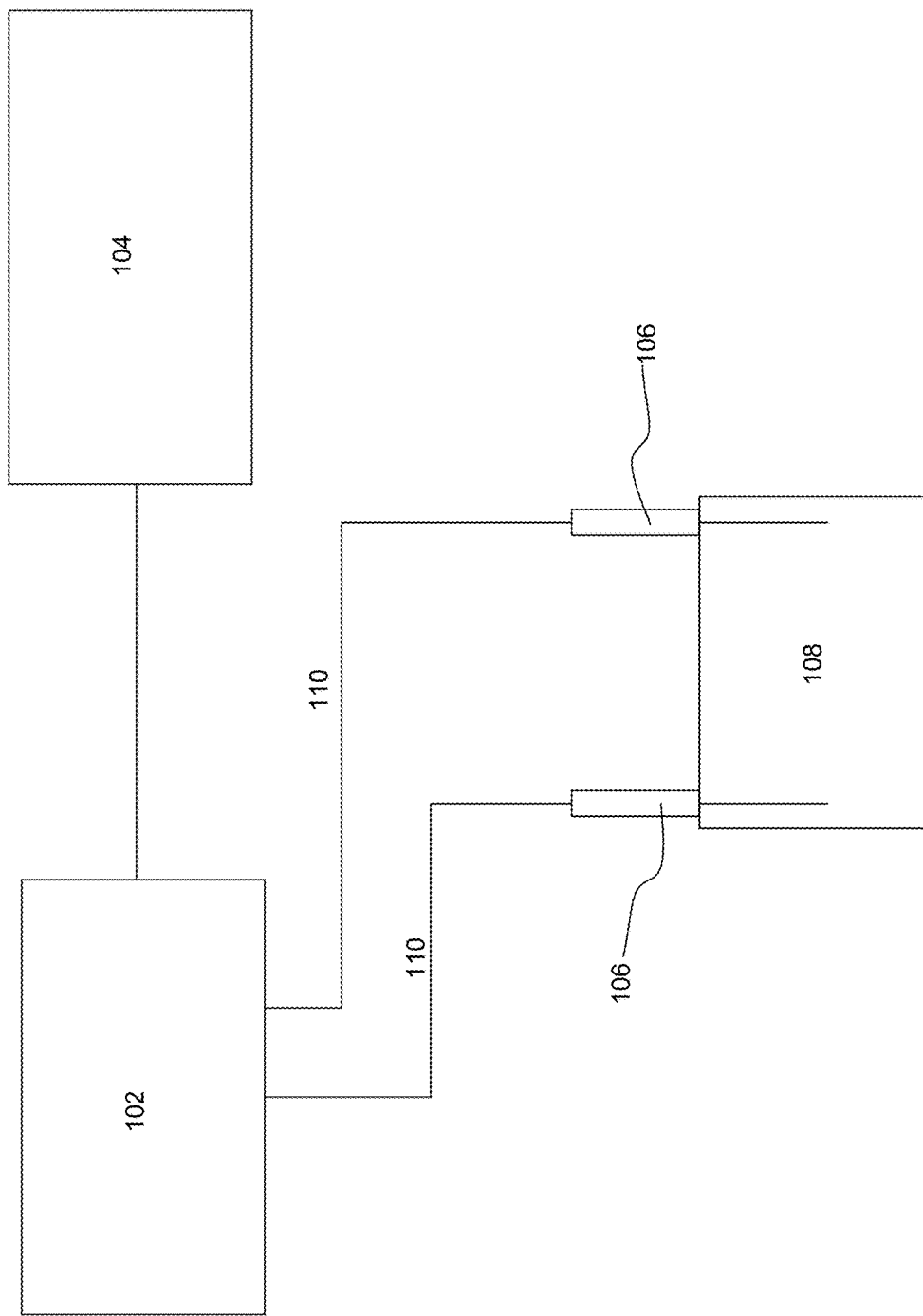
FIG. 1 shows a radio frequency measurement system.

The present disclosure is based on the recognition that conventional coaxial cables can be terminated with an antenna or probe end, without the need for ancillary interconnects and related components. The disclosure addresses the need for robust radio frequency antennas or probes which exhibit low inherent variability, and through their design, reduce operator-induced errors when the probes are installed, removed, or replaced. Probe designs with enhanced functionality are also disclosed, which permit the measurement of more than one parameter from a single antenna.

Throughout this disclosure, it should be noted, that the terms radio frequency "probe" or "antenna" are used interchangeably and intended to describe the same system, namely a device which is, at a minimum, capable of transmitting or receiving a radio frequency signal. The frequency range is intended to span from KHz to THz, depending on the application, with preferred frequencies in the MHz to GHz range for certain applications. Similarly, the terms "radio frequency" and "microwave" are used interchangeably in this disclosure to describe signals with frequencies from the KHz to THz range.

One application in particular includes radio frequency or microwave systems for monitoring the state of emission control devices. Diesel and gasoline particulate filters represent one category of emission control devices to which radio frequency sensing is applied to monitor soot and ash levels in the filter. Catalytic emission control devices, such as three-way catalytic converters, oxidation catalysts, selective catalytic reduction systems, and lean NOx traps, among others, represent another category of emission control devices to which radio frequency sensing may be applied to monitor parameters related to the state or function of the device, such as the amount of various adsorbed gaseous components (oxygen, nitrogen oxides, ammonia, and others).

Other applications include any type of cavity measurement systems, such as cavity perturbation measurement systems. In yet another embodiment, the antenna may be operated in free space, without the need for a cavity. Another embodiment may be the integration of the antenna in a transmission line.

The antennas used in some of these applications must be capable of withstanding high exhaust temperatures, oftentimes in excess of 600° C., must be sealed to prevent the escape of exhaust gases to the environment, must withstand high vibration levels, exposure to the elements, harsh chemical environments, and a number of additional demanding requirements. Furthermore, the antennas must be easily installed during the factory assembly process, and also be readily serviceable and replaceable in the field with minimal impact on the measurement system performance.

The challenges associated with these demanding requirements are many, particularly when considering component size and cost constraints. In applications such as radio frequency systems used to monitor the state of emission control devices, where the metallic housing of the emission control devices serves as a microwave resonant cavity, the measurement can be very sensitive to the antenna design, location, and orientation of the antenna in the housing. Cables and interconnects between the radio frequency transmitter and receiver and the antennas can introduce losses, reflections, phase shift, and other variables which affect the signal and resulting measurement, in addition to increased costs and reliability issues. The present disclosure reduces or eliminates these sources of variability in the system.

The presence of interconnects, in particular near transitions to components subject to high levels of vibration, also introduces the possibility of loosening over time, or introducing additional sources of variability into the system. Moisture intrusion, corrosion, the degradation of the connector through high temperatures, and related deleterious effects are a concern. In addition, the use of an interconnect also provides easy access to disable the sensing or measurement system, in some cases.

Furthermore, a number of sensors are generally installed on the afore-mentioned emission control devices, including temperature sensors, pressure sensors, gaseous composition sensors (oxygen sensors, NOx sensors, and the like), soot sensors, and related sensors, in addition to the radio frequency antennas. In addition, accurate radio frequency measurements of the state of the emission control device often requires input from one or more sensors, such as temperature measurements, in one example, to compensate or correct the radio frequency signal in cases where cross-sensitivities to other parameters exist. In a particular example, soot level determination in diesel or gasoline particulate filters through radio frequency means requires temperature compensation to correct for the variation in the dielectric properties of the soot with temperature. However, many applications of radio frequency sensing require similar methods to compensate for variations in temperature or other parameters. Aside from temperature, other parameters or conditions may also influence cavity resonance measurements or antenna measurements and must be known or monitored in order to improve the RF measurements.

The present disclosure also describes a radio frequency probe capable of measuring one or more parameters, in addition to transmitting or receiving a radio frequency signal. In this manner, the same probe may be used to monitor one or more parameters, thereby eliminating the need for other sensors. The parameters monitored by the probe need not be the same parameters for which compensation of the radio frequency signal is required. For example, a probe may be configured to monitor temperature and pressure, in addition to transmitting or receiving a radio frequency signal, even though the radio frequency signal only requires temperature compensation. In this case, the pressure measurement may serve some other purpose, which may or may not be related to the radio frequency measurement. In yet another example, the radio frequency probe may be configured to monitor temperature and a gaseous emissions component.

While examples have been given related to emission control systems and devices, the radio frequency probes described herein are equally applicable to a number of applications ranging from laboratory instruments and medical devices, to process control systems, chemical reactors, sensors, and even wireless signal transmission. The probes may be mounted in a radio frequency cavity, a wave guide, or used in systems transmitting radio frequency signals through free space. Applications requiring robust antennas with low variability or antennas capable of monitoring one or more parameters, in addition to transmitting or receiving radio frequency signals, will all benefit from the present apparatus.

The apparatus will now be described in conjunction with the figures. With reference first to FIG. 1, one embodiment of a radio frequency sensing system includes a radio frequency control unit 102 in communication with a process control unit 104, one or more radio frequency probes 106, a microwave resonant cavity 108, and cables 110. The radio frequency control unit 102 may contain a radio frequency transmitter, receiver, and related components required to conduct the radio frequency measurements. The process control unit 104 may be an engine control unit or any other suitable process control unit, but may or may not be required, depending on the application. One or more radio frequency probes 106 may be in communication with the radio frequency control unit 102 through one or more cables 110. In one embodiment a cable 110 may be integrated into radio frequency probe 106 without the use of any additional connectors. The radio frequency probe 106 may be a rod antenna, loop antenna, waveguide, or any other suitable means for transmitting or receiving a radio frequency signal. Microwave resonant cavity 108 may be catalyst housing or particulate filter housing in one example, and may or may not contain inlet or outlet portions to enable material to enter or exit the cavity. Microwave resonant cavity 108 may or may not be required depending on the application. In another embodiment, radio frequency control unit 102 may be integrated directly into radio frequency probe 106 without use of cable 110. In yet another embodiment, process control unit 104 may be integrated into radio frequency control unit 102 or vice versa. One or more interconnects may be used along the length of cable 110 between radio frequency control unit 102 and radio frequency probe 106 or no interconnects may be used. Cable 110 may be a coaxial cable, twisted pair, may or may not contain shielding, or may be another other single or multi-conductor cable.

Radio frequency probe 106 may or may not contain additional sensing elements such as temperature sensors (thermocouple, thermistor, RTD, fiber optic), pressure sensors, strain gauges, gas sensors, moisture sensors, accelerometers, position sensors, and the like, generically referred to as ancillary sensors. One or more ancillary sensors may be integrated into radio frequency probe 106 to provide independent measurements of parameters or state variables in addition to the radio frequency signal which may be transmitted or detected by radio frequency probe 106. The ancillary sensing electronics, such as a thermocouple or RTD circuit chip, (integrated circuits such as those produced by Maxim in one example), pressure sensing electronics, signal conditioning, wheatstone bridges, and the like may also be contained in radio frequency control unit 102 or process control unit 104 or radio frequency probe 106. The signals from ancillary sensors may be transmitted through additional conductors or the same conductors contained in cable 110. In the case where the same cable is used, as series of switches in radio frequency control unit 102 may be used to alternately isolate the radio frequency signal and electronics from the ancillary sensing signal and electronics. In another embodiment, additional cables for the ancillary sensors may be used or additional conductors in cable 110 may be used.

Figure 2A:
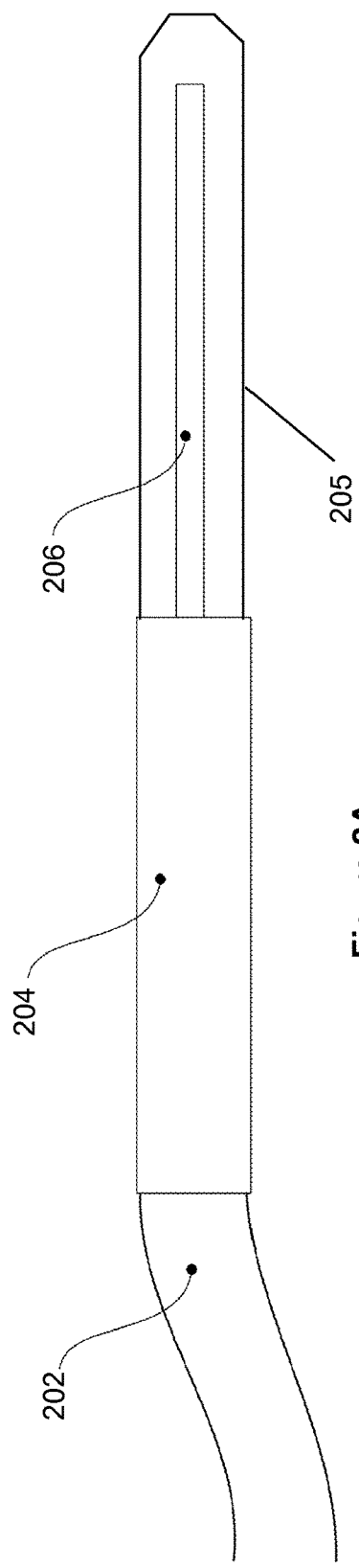
FIG. 2A shows a coaxial cable with an integrated antenna.

FIG. 2A presents one exemplary embodiment of radio frequency probe 106 shown in FIG. 1. The probe in FIG. 2A includes a coaxial cable 202, outer sleeve 204, and inner conductor 206. The outer sleeve 204 and the inner conductor 206 are both made of a conductive material. The outer sleeve 204 and inner conductor 206 may or may not be of the same material. In one embodiment outer sleeve 204 and inner conductor 206 may be copper, gold, silver, steel, aluminum, stainless steel or similar alloys, such as inconel, but any suitable material may be used. In another embodiment, outer sleeve 204 and inner conductor 206 may be fully or partially encased or enclosed in a non-conductive material 205, such as ceramic, glass, plastic (for low temperature applications) or the like. The casing may serve to prevent contamination of the probe or otherwise physically separate inner conductor 206 or outer sleeve 204 from the surrounding environment, but still permit transmission or reception of a radio frequency signal. The encasing non-conductive material 205 may or may not be porous.

Although shown as a tube, the outer sleeve 204 can have different topologies: it can be contoured or corrugated, have groves or ridges, as in helically or spirally corrugated conductor, or bellow-like shape. Similarly, inner conductor 206 can have multiple cross sections.

Figure 2B:
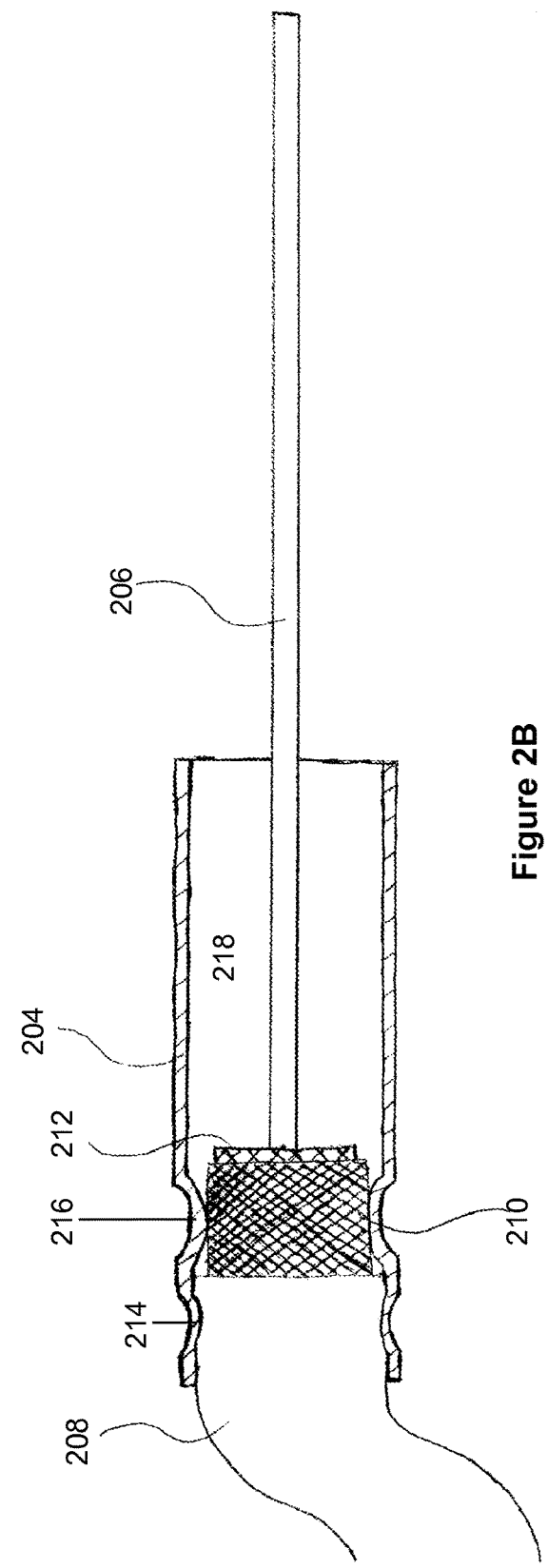
FIG. 2B is cross-sectional view of an antenna integrated with a coaxial cable.

Addition details of the probe assembly are shown in the cut-away view in FIG. 2B. Outer sleeve 204 may be connected to outer insulating jacket 208 of coaxial cable 202 by means of a mechanical or chemical bond or connection. In one embodiment, outer sleeve 204 may be connected to the outer insulating jacket 208 by means of one or more second crimp connections 214. Adhesive or sealant (not shown) may or may not be used to facilitate the connection. In this manner, a conventional coaxial cable may be terminated with an antenna probe connection, suitable for transmitting or receiving radio frequency signals.

The coaxial cable 202 includes an outer insulating jacket 208, and a coaxial braid 210. The coaxial cable 202 may be RG58 or RG400 or any other type of coaxial cable meeting the application requirements. Additionally, as shown in FIG. 2C, the coaxial cable 202 also comprises an inner dielectric material 220 disposed between the inner conductor 206 and the coaxial braid 210. An inner sleeve 212 is also shown, inserted below the coaxial braid 210. The inner sleeve 212 is preferably a rigid, cylindrical, and electrically conducting material. In one embodiment, the inner sleeve 212 has an inner diameter the same as that of the coaxial braid 210, however the diameter may be larger or smaller in other embodiments. The inner sleeve 212 may or may not be knurled or contain other surface features (roughness, threads, spirals, ridges or the like) to increase the contact area and facilitate a robust connection between the inner sleeve 212 and the coaxial braid 210. Further, the inner sleeve 212 may or may not be connected to outer sleeve 204.

FIGS. 2C and 2D present another embodiment showing additional details and a cut-away view of a system in which outer sleeve 204 contains an integrated inner sleeve portion 212 as a single component. In this embodiment, the inner diameter 222 of inner sleeve portion 212 may or may not be the same as inner diameter 224 of the outer sleeve portion 204. Further, in this embodiment, inner sleeve portion 212 is inserted below coaxial braid 210 but above inner dielectric material 220 of coaxial cable, as shown in FIG. 2D. FIG. 2C shows a first step in which outer sleeve 204 is first positioned over inner conductor 206 and before coaxial braid 210, and FIG. 2D presents a second step where inner sleeve 212 is slid below coaxial braid 210 prior to crimping.

Once assembled, the outer sleeve 204 is crimped over the inner sleeve 212 with first crimp connections 216 and over the outer insulating jacket 208 with second crimp connections 214. A variation not shown in FIG. 2B has the inner sleeve 212 as integral part of the outer sleeve 204, with first crimp connections 216 and second crimp connections 214 being as a separate sleeve, allowing for ease of placement of the coaxial braid 210 over the inner sleeve 212.

In one example, crimped portion of outer sleeve 204 may be separate from the remainder of outer sleeve 204. In another embodiment, inner sleeve 212 may be a separate component from outer sleeve 204 prior to assembly, but may be in electrical contact with outer sleeve 204 following assembly.

In another embodiment, the inner sleeve portion 212 may have an inner diameter 222 equivalent to that of the inner diameter of the coaxial braid 210 and the inner diameter 224 of the outer sleeve portion 204. In one embodiment, the inner diameters 222, and 224 and the inner diameter of coaxial braid 210 may be configured to ensure correct impedance matching of the outer sleeve 204 to the coaxial cable 202. In another embodiment, the impedance matching may be affected by the inner diameters 222, and 224 and the inner diameter of coaxial braid 210 and by the inner dielectric material 220 of the coaxial cable 202 and any dielectric material located within the region bounded or enclosed by outer sleeve 204. In one example, the ratio of the inner diameter 224 of outer sleeve 204 to the outer diameter of inner conductor 206 may be approximately 2.3:1. In yet another example, the ratio of the inner diameter 224 of outer sleeve 204 to the outer diameter of inner conductor 206 may be a function of the dielectric material fully or partially contained within outer sleeve 204, designated as cavity 218 in FIG. 2. The impedance match may be for a 50 Ohm or 75 Ohm cable or any other impedance.

Regardless of whether inner sleeve 212 is connected to outer sleeve 204 (as in FIGS. 2C and 2D) or not connected to outer sleeve 204 (as in FIG. 2B), the inner sleeve 212 serves as a rigid support to ensure good electrical contact between the outer sleeve 204 and the coaxial braid 210 of the coaxial cable 202. In one embodiment, a first crimp connection 216 (see FIG. 2B) may be used to mechanically compress outer sleeve 204 onto coaxial braid 210, which is supported internally by inner sleeve 212. In this manner, electrical continuity is ensured between the coaxial braid 210 and outer sleeve 204 of the probe.

One or more second crimp connections 214 (see FIG. 2B) may be made to secure outer sleeve 204 to outer insulating jacket 208 of coaxial cable 202. The second crimp connections 214 may or may not be required. Adhesives or other suitable bonding or sealing agents may also be applied to enhance the strength of the connection between outer insulating jacket 208 of coaxial cable 202 and outer sleeve 204. Many crimping options exist; for example, a hexagonal crimping tool can be used for performing the crimping operations, or other tools or crimping methods.

The region between inner conductor 206 and outer sleeve 204, identified as cavity 218, in FIG. 2B, may or may not be filled with a suitable dielectric material. In one embodiment, high temperature mat material, such as intumescent fibers, may be used to completely or partially fill cavity 218. In a particular embodiment, the material may exhibit similar characteristics to intumescent mounts produced by 3M and commonly used for mat mounts in particulate filter and catalysts assemblies. In another embodiment, the material may be non-intumescent. Various other materials including ceramics, glass, polymers, and related materials may also be used to completely or partially fill cavity 218, depending on the requirements of the application.

The addition of material to cavity 218 serves several purposes. First, it ensures that inner conductor 206 remains centered in outer sleeve 204. Second, it increases the strength of the overall probe assembly, and prevents loosening of inner conductor 206 from the probe assembly. Third, it may act to form a seal and prevent introduction of foreign matter, including gases, liquids, or other solid matter into probe assembly.

Inner conductor 206 may be integral to the coaxial cable 202, such that it is the central conductor of the cable assembly. Inner conductor 206 may or may not be of the same material as the coaxial braid 210. In one embodiment, outer insulating jacket 208, coaxial braid 210, and inner dielectric material 220 may be stripped to expose a specified length of inner conductor 206. In another embodiment, inner conductor 206 may be fully- or partially encased in a sheath, which may or may not be conducting. The sheath may serve to reinforce and protect inner conductor 206.

FIGS. 3A-C depict a series of steps to better illustrate the details of the assembly and construction of the coaxial cable with integral radio frequency probe. With reference now to FIG. 3A, one end of a coaxial cable 202 is shown, which includes an outer insulating jacket 208, a coaxial braid 210, an inner dielectric material 220, and an inner conductor 206.

First, the coaxial cable 202 is stripped to reveal the internal components, namely coaxial braid 210, inner dielectric material 220, and inner conductor 206. In one embodiment, the coaxial cable 202 is stripped such that the inner conductor 206 is exposed and of a sufficient length to be as long, or slightly longer than the desired inner conductor sheath 312 of the antenna. Inner conductor sheath 312 may be copper, aluminum, stainless steel, steel, iron silver, or gold, inconel or any other suitable material. Inner conductor sheath 312 may be a tube and may or may not be conducting. Next, inner sleeve 212, which may or may not be knurled or exhibit a textured surface, is slid over exposed inner conductor 206 and inner dielectric material 220 but under coaxial braid 210, such that coaxial braid 210 covers all or nearly all of inner sleeve 212.

In a following step, shown in FIG. 3B, inner conductor sheath 312 of the antenna is slid over inner conductor 206 of coaxial cable 202. In one embodiment, inner conductor sheath 312 is a metallic tube (composed of suitable metal alloy, such as a type of stainless steel or any other suitable alloy), which may or may not be closed at one end, with an inner diameter similar to that of the outer diameter of inner conductor 206. Inner conductor sheath 312 may or may not be fastened to inner conductor 206 by crimping at one or both ends or anywhere along the length of inner conductor sheath 312. In another embodiment, high temperature solder, brazing, or welding is used, to join inner conductor sheath 312 to inner conductor 206. In yet another embodiment, connection of inner conductor sheath 312 and inner conductor 206 is facilitated by first heating inner conductor sheath 312 to increase the internal diameter of inner conductor sheath 312 by means of thermal expansion, before sliding inner conductor sheath 312 over inner conductor 206. Many other methods may also be used to join inner conductor 206 and inner conductor sheath 312.

In another embodiment, inner conductor 206 may extend fully through inner conductor sheath 312, such that inner conductor 206 protrudes from the distal end of inner conductor sheath 312. In this embodiment, inner conductor 206 may be folded over, flattened, or otherwise formed into a shape or position to prevent inner conductor sheath 312 from sliding off inner conductor 206.

The addition of inner conductor sheath 312 over inner conductor 206 serves to increase the rigidity of inner conductor 206, and also acts as a protective sheath, thereby protecting inner conductor 206 from harsh environments. Further, completely surrounding inner conductor 206 by the protective sheath formed by inner conductor sheath 312 provides a large amount of surface area to ensure good electrical contact between inner conductor 206 and inner conductor sheath 312.

In a following step shown in FIG. 3C, outer sleeve 204 is slid over inner conductor 206 and over exposed coaxial braid 210. In another embodiment (not shown), inner sleeve 212 may be integrated into outer sleeve 204 such that the two individual components shown in FIG. 3A form a single component exhibiting the same functionality and features of the two individual components. FIG. 3B shows inner sleeve 212 positioned under coaxial braid 210 but over the inner dielectric material 220. Inner sleeve 212 may or may not be connected to outer sleeve 204.

In FIG. 3C, outer sleeve 204 is shown positioned over exposed coaxial braid 210, and may or may not extend over a portion of the outer insulating jacket 208. In a first step, with reference to FIG. 3C, outer sleeve 204 is fixed to coaxial cable 202 by means of one or more crimp connections, with at least one first crimp connection 216 positioned over exposed coaxial braid 210 and inner sleeve 212 such as to create a secure mechanical connection between coaxial cable 202 and outer sleeve 204, and to create an electrically conducting path between coaxial braid 210 and outer sleeve 204. Adhesives, sealants, or other type of bonding materials may or may not be applied to further fix outer sleeve 204 to coaxial cable 202.

It should be noted that outer sleeve 204 need not extend beyond exposed coaxial braid 210 in some embodiments. In a particular embodiment (not pictured), exposed coaxial braid 210 and inner dielectric material 220 may extend through the full length of outer sleeve 204. In this embodiment, internal diameter of outer sleeve 204 may be of nominally the same diameter, or slightly larger, than the outer diameter of coaxial braid 210. Inner sleeve 212 may or may not be used in this embodiment, or in any of the aforementioned embodiments. In yet another embodiment, coaxial braid 210 may extend the full length of outer sleeve 204 but inner dielectric material 220 may not. These particular variations of the embodiment depicted in FIG. 3, namely variations in the length of coaxial braid 210 and inner dielectric material 220 within outer sleeve 204 may be preferred in some cases.

The fully-assembled radio frequency probe is shown in FIG. 3C, which includes outer sleeve 204 securely fastened to coaxial braid 210 and outer insulating jacket 208, as well as inner conductor 206 completely encased in inner conductor sheath 312. In cases where coaxial braid 210 and inner dielectric material 220 do not extend to the end of outer sleeve 204, the void cavity formed between the outer diameter of the inner conductor sheath 312 and the inner diameter of the outer sleeve 204 may or may not be fully- or partially-filled with a dielectric, insulating, or sealing material. Further, the geometry of the probe assembly shown in FIG. 3, in particular the selection of the inner diameter of outer sleeve 204, outer diameter of the inner conductor sheath 312, and the dielectric, insulating, or sealing material contained in the region bounded thereby (if present) should be selected to match the impedance of the system for which the antenna probe and cable assembly will be used. In one embodiment, an impedance of 50 ohms is used, although any impedance may be used such that it matches the design specifications of the system.

FIGS. 4A and 4B present additional details of a particular embodiment of a radio frequency probe according to the present invention. The embodiment includes a coaxial cable 402, external sealing component 404, outer sleeve 406, exposed coaxial outer braid 408, inner sleeve 410, sealing or adhesive compound 412, mating components 414 and 416 and inner conductor 418. External sealing component 404 may or may not be used. In one embodiment, external sealing component 404 is a heat shrink tube, sealing tape, or other suitable component for forming a seal around coaxial cable 402 and outer sleeve 406. External sealing component 404 may or may not facilitate heat transfer. Internal sealing or adhesive compound 412 may or may not be used. In one embodiment, internal sealing or adhesive compound 412 may be a one- or multi-part epoxy, silicone, polymer, or similar material, used to enhance the strength and stability of the transition between the inner conductor of the coaxial cable (not pictured) and the inner conductor 418.

An interface consisting of two mating components 414 and 416 is also shown, which enables connection of the radio frequency probe to the measurement system. In one embodiment, mating components 414 and 416 may form a conventional compression fitting. In another embodiment, mating components 414 and 416 may form a conventional threaded fitting. In yet another embodiment, mating components 414 and 416 may not be threaded at all, but allow for a secure connection using any number of conventional means. In yet another embodiment, mating components 414 and 416 may not be used at all, and outer sleeve 406 may be fixed to surface 420 by soldering, welding, or any other means.

In one embodiment, mating component 416 may be permanently fixed to the measurement system, such as surface 420. Mating component 414 may be allowed to freely rotate around outer sleeve 406. A flange, ferule (such as with a conventional compression fitting), or other rigidly mounted stop may also be attached to outer sleeve 406 or integrated into the receiving mating component 416 to ensure correct antenna alignment and insertion depth. In another embodiment, mating component 416 may contain a through hole of two different diameters to provide an internal stop. Integration of such features prevents errors induced by incorrect antenna installation, or improperly tightening the connection. Such errors are not easily avoided with the use of only simple threaded connections. Further, allowing mating component 414 to freely rotate around outer sleeve 406 prevents rotation of outer sleeve 406 and coaxial cable 402 during probe removal and installation.

FIG. 5A is a probe with integrated ancillary sensor 514, including outer insulating jacket 502, coaxial braid 506, first and second adapter rings 504 and 516, outer sleeve 508, inner conductor sheath 510, inner conductor 512, where integrated ancillary sensor 514 is wrapped around inner conductor 512 and contained within inner conductor sheath 510. The integrated ancillary sensor 514 may be any type of sensor. FIG. 5B shows a similar probe without an integrated ancillary sensor, but with the first and second adapter rings 504 and 516. Wrapping ancillary sensor 514 around inner conductor 512 ensures tight and continuous contact with inner conductor sheath 510 enhancing the mechanical rigidity and fit. While the ancillary sensor 514 is shown as wrapped around inner conductor 512, other embodiments are possible, where the ancillary sensor 514 is disposed proximate the inner conductor 512.

Figure 6A:
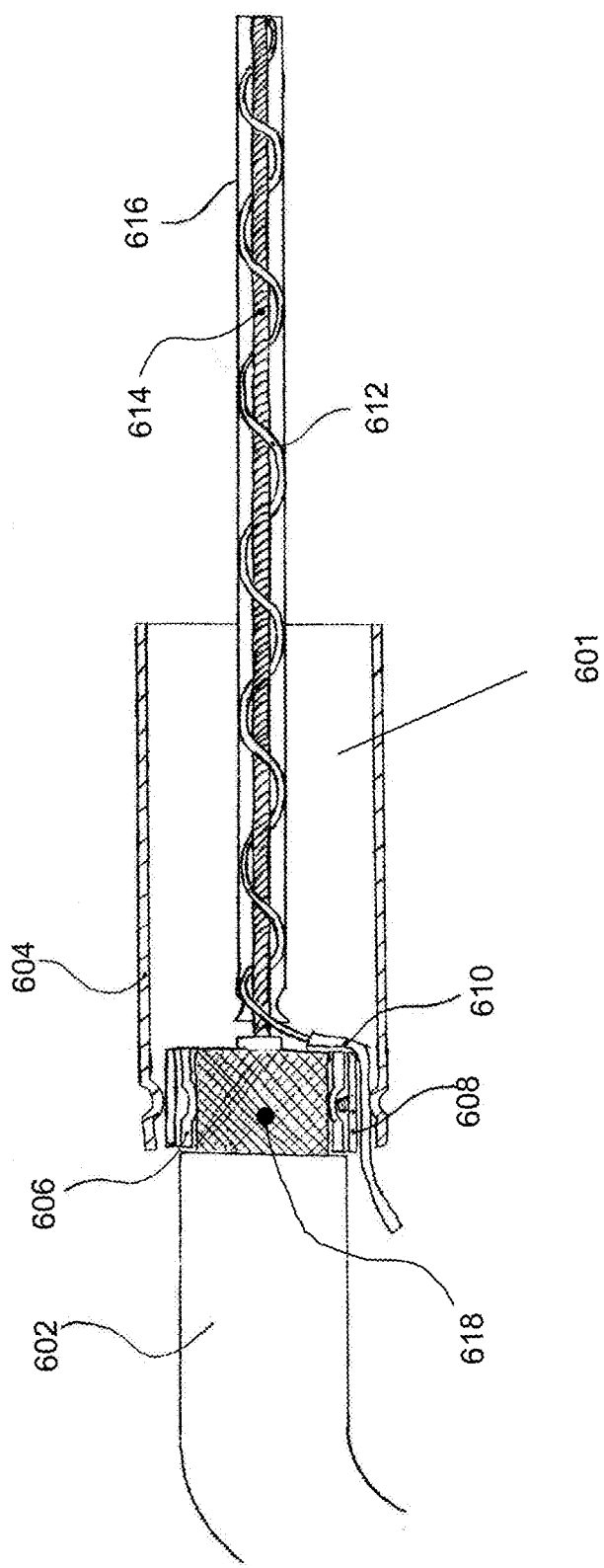
FIG. 6A is a cross-sectional view of an antenna probe integrated with a coaxial cable containing a second sensing element.

A radio frequency probe with an integrated temperature sensor is shown in FIG. 6A. The probe is capable of transmitting and receiving radio frequency signals and measuring temperature near the tip of the probe. The probe includes a coaxial cable 602, an outer sleeve 604 in electrical contact with an exposed portion of the coaxial braid 618, a series of concentric spacer rings 606 and 608, an insulated covering 610, an ancillary sensor 612, such as a thermocouple or other sensor, an inner conductor 614, and an inner conductor sheath 616.

Concentric spacer rings 606 and 608 may or may not be required. The concentric spacer rings 606 and 608 enable the transition from the coaxial cable 602 to an outer sleeve 604 of larger internal diameter than the coaxial braid 618, while still maintaining electrical contact between the coaxial braid 618 and outer sleeve 604. In addition, concentric outer spacer ring 608 contains a slit to allow ancillary sensor insulating sheath 610 and ancillary sensor 612 to pass through. One or more ancillary sensors 612 may be integrated into the radio frequency probe shown in FIG. 6A in this manner. The diameter and thickness of the concentric spacer rings 606 and 608 may be suitably chosen to form the required transition from the outer diameter of the coaxial braid 618 to the inner diameter of the outer sleeve 604. In some embodiments, only one spacer ring may be required, and in other embodiments, no spacer rings may be required.

In the embodiment shown in FIG. 6A, the concentric inner spacer ring 606 is crimped onto the coaxial braid 618. Not pictured is an inner sleeve below the braid, such as inner sleeve 212 in FIG. 3, which may or may not be required. Concentric outer spacer ring 608 contains a slit allowing ancillary sensor insulating sheath 610 to pass through. Outer sleeve 604 is shown crimped on to concentric outer spacer ring 608.

Ancillary sensor insulating sheath 610 is used to prevent electrical contact between a metallic ancillary sensor 612 (such as a thermocouple or RTD sheath in one embodiment, with a particular example being a type K thermocouple with an outer sheath diameter between 0.0.1" to 0.125") and the coaxial braid 618 or outer sleeve 604. The ancillary sensor insulating sheath 610 may be conventional heat shrink tubing, fiber glass wool, a polymer coating, or any other suitable insulating material.

Ancillary sensor 612 may include a single sheath containing thermocouple wires (not pictured) for any type of thermocouple, with a preferred type being Type K, and a preferred sheath material being inconel (or any suitable alloy), however, any type of appropriate thermocouple and sheath may be used. In one embodiment, the diameter of ancillary sensor 612 ranges from 0.01 to 0.062 inches, but may be larger or smaller in other cases. An example of such a sensor is the KMQXL-020-12 thermocouple sold by Omega, however any suitable thermocouple of similar design may be used. In another embodiment, the ancillary sensor 612 is an RTD sensor, thermister, pressure sensing element, strain gauge, or any other ancillary sensor.

Ancillary sensor 612 may be wrapped around inner conductor 614 contained within inner conductor sheath 616. Ancillary sensor 612 may extend to the end of inner conductor sheath 616 or any desired intermediate position within inner conductor sheath 616. In the case of a thermocouple or RTD, the sensing junction or location in ancillary sensor 612 is at the tip or end of the ancillary sensor 612 or at any other preferred position. Ancillary sensor 612, inner conductor 614 and inner conductor sheath 616 may be joined by crimping at one or both ends, or some intermediate position, or other mechanical or chemical means, such a by glue, solder, brazing, or other suitable means. Inner conductor sheath 616 may or may not be fully or partially filled with a material to enhance the bond between inner conductor sheath 616, ancillary sensor 612, and inner conductor 614.

In another embodiment, ancillary sensor 612 need not be contained within inner conductor sheath 616 but may be wrapped around the exterior surface of inner conductor sheath 616 or run parallel to inner conductor sheath 616. In yet another embodiment, ancillary sensor 612 may not be in contact with inner conductor 614 or inner conductor sheath 616 at all, but attached at any position along the inner surface of outer sleeve 604. In the case where ancillary sensor 612 is positioned along or extending from the inner surface of outer sleeve 604, ancillary sensor insulating sheath 610 and concentric spacer rings 606 and 608 may not be required, thereby simplifying the system.

The end of ancillary sensor 612 extending from the antenna assembly may be connected to any type of suitable connector or cable assembly (not shown) in one embodiment. In another embodiment, the cable connected to ancillary sensor 612 may be wrapped around the coaxial cable 602 to form an integrated ancillary sensor and coaxial cable assembly (also not shown) or a multi-conductor cable may be used.

Outer sleeve 604 may or may not extend past exposed coaxial braid 618. In one embodiment, outer sleeve 604 may extend beyond exposed coaxial braid 618 and be mechanically or chemically fastened or bonded to coaxial cable 602. Heat shrink or other type of sealing material may be used to seal the connection between outer sleeve 604 and coaxial cable 602 (not shown).

In yet another embodiment, ancillary sensor 612 may exit outer sleeve 604 through a hole located on the side of outer sleeve 604, in which case, concentric spacer rings 606 and 608 may or may not be required. The hole may or may not be sealed with a sealing compound or covered such as by a heat shrink tube or other similar covering.

Figure 6B:
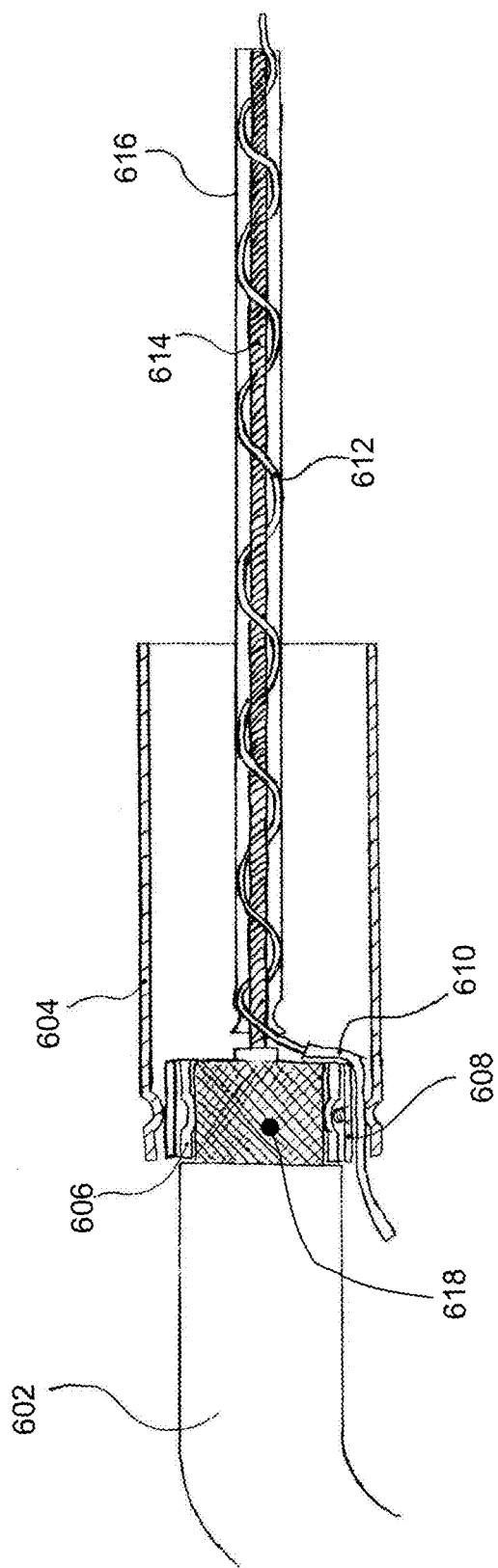
FIG. 6B is a cross-sectional view of an antenna probe integrated with a coaxial cable containing a second sensing element extending from the end of the antenna.
Figure 6C:
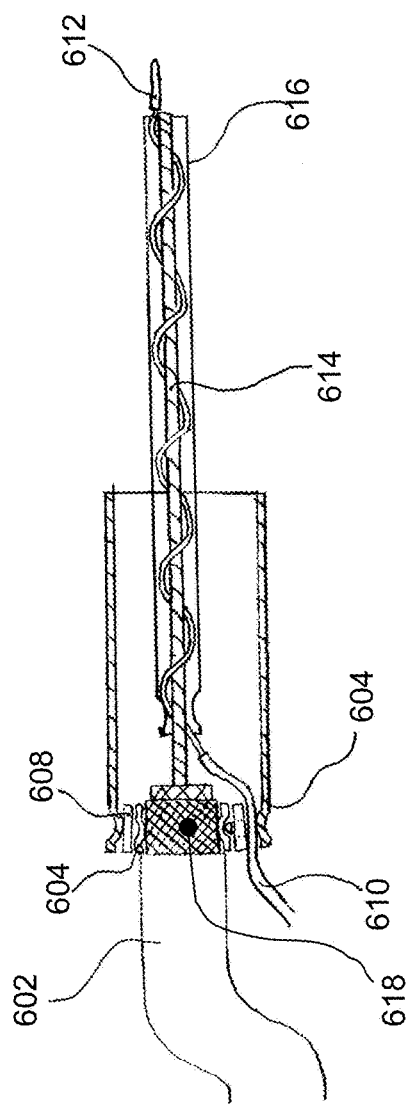
FIG. 6C is a cross-sectional view of an antenna probe integrated with a coaxial cable containing a second sensing element extending from the end of the antenna.

FIG. 6B presents another embodiment, where ancillary sensor 612 extends from the end of inner conductor sheath 616. Yet another embodiment is shown in FIG. 6C where ancillary sensor 612 is a resistance temperature detector (RTD) or similar sensor which extends from the end of inner conductor sheath 616. Ancillary sensor 612 need not be a thermocouple or RTD at all, but may be any type of sensing element, including an optical fiber or probe.

Figure 7:
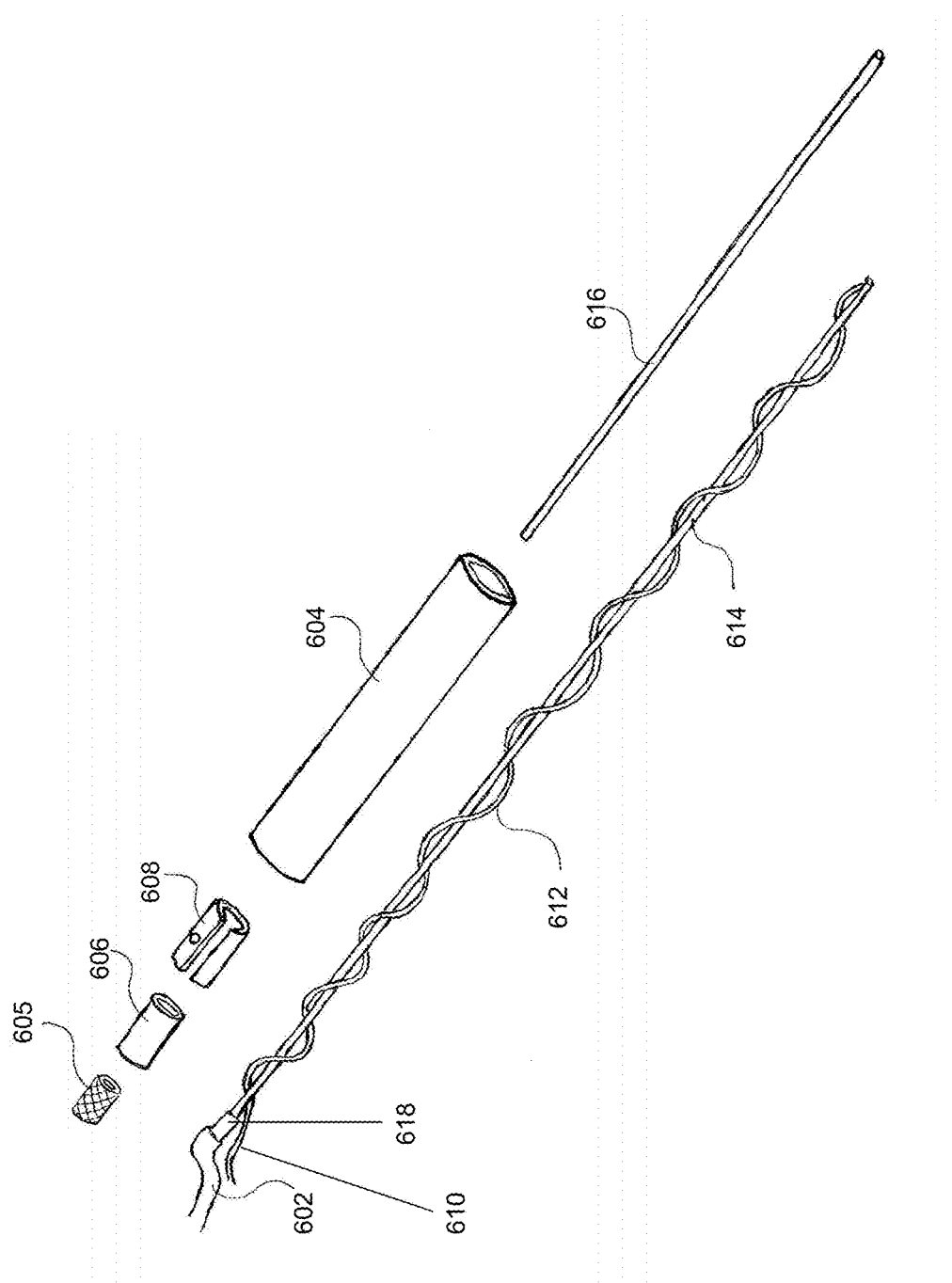
FIG. 7 is an exploded view of the components used to assemble an antenna probe integrated to the end of a coaxial cable, having a second sensing element.

An exploded view of the major components comprising the radio frequency probe with integrated temperature sensing element is shown in FIG. 7. The components include a coaxial cable 602 with an exposed inner conductor 614 and exposed coaxial braid 618, an ancillary sensor 612 wound around inner conductor 614, a crimp support 605, concentric inner spacer ring 606 and concentric outer spacer ring 608, outer sleeve 604 and inner conductor sheath 616. Not all the components shown in FIG. 7 are required, depending on the specific design and application. For example, crimp support 605 and concentric spacer rings 606 or 608 may not be required.

Concentric outer spacer ring 608 shows additional details, including the slit to allow ancillary sensor 612 to pass through to the exterior of outer sleeve 604. Electrical isolation of ancillary sensor 612 is provided by ancillary sensor insulating sheath 610. A small hole is also shown in concentric outer spacer ring 608 which may be used for a set screw or other suitable fastener (not pictured) to be used to firmly connect the concentric spacer rings 606 and 608 and ensure good electrical contact between the coaxial braid 618 of the coaxial cable and concentric spacer rings 608 and 606. Any type of connection, including crimp connections, solder or brazed connections, or other mechanical or chemical (adhesives, sealants) may be used to join outer sleeve 604 to exposed coaxial braid 618 or coaxial cable 602. Crimp support 605 may or may not be used.

It should be noted however, that the inner conductor 614 and ancillary sensor 612 may be reversed such that inner conductor 614 is wrapped around ancillary sensor 612, within inner conductor sheath 616. In another embodiment, inner conductor 614 and ancillary sensor 612 may both be twisted about one another. Additional ancillary sensors may be twisted together in this manner and encased in inner conductor sheath 616. In one embodiment, different types of ancillary sensors 612 may be used, and each ancillary sensor 612 may or may not have the same length within inner conductor sheath 616.

The void space within inner conductor sheath 616 not occupied by ancillary sensors 612 or inner conductor 614 may or may not be filled with dielectric material, ceramic powder, conductive material, or the like in order to improve rigidity and mechanical strength of the inner conductor sheath 616. The addition of dielectric material, sealant, spacer rings, spirally wound spacer, or other packing material into region 601, shown in FIG. 6A, serves a number of benefits. First it provides additional mechanical and structural stability to fix the position of the inner conductor sheath 616 containing ancillary sensor 612 and inner conductor 614 within outer sleeve 604. Second, it may provide additional isolation and sealing of the ancillary sensor insulating sheath 610 from the outer sleeve 604 and inner conductor sheath 616. Different types of material may be utilized to pack or fill region 601. In one example, the back 5%-25% of the region 601 may be filled with a sealant or epoxy (nearest the coaxial cable 602) with the remaining volume filled with a high temperature fibrous matting material or ceramic, in one embodiment. The sealant may fix the ancillary sensor insulating sheath 610 in place, preventing chafing or wearing away of the insulating material and also form an impervious seal to prevent the leakage of liquids, solids, or gases.

Figure 8:
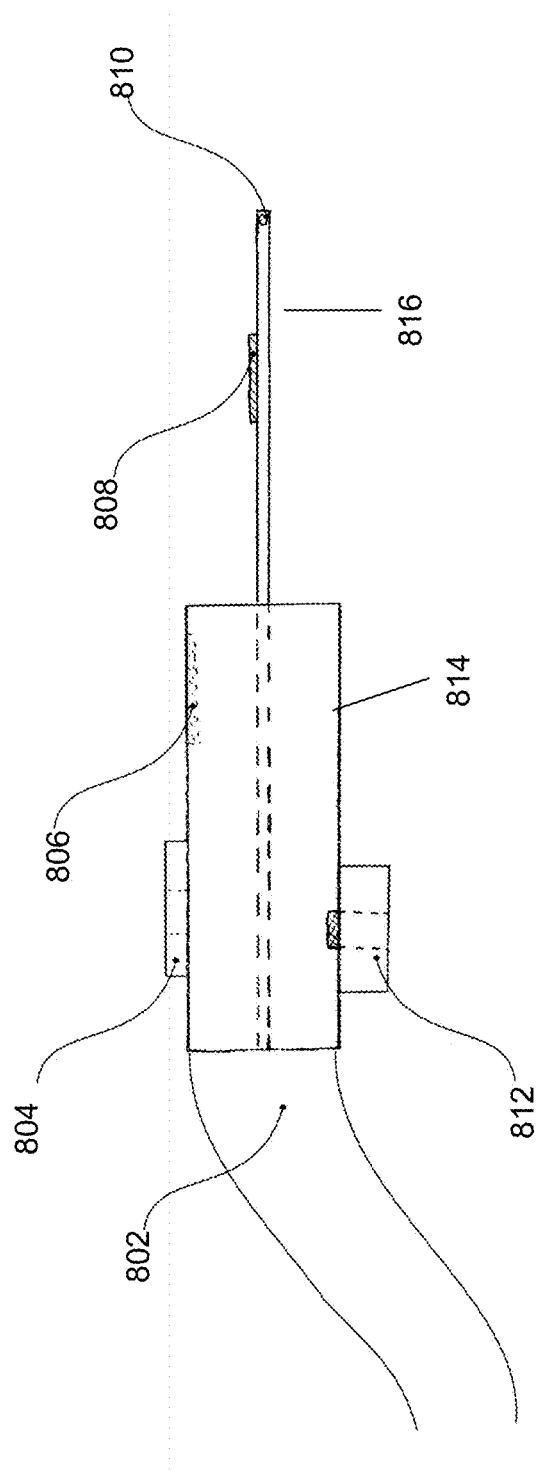
FIG. 8 is a radio frequency probe containing various sensing elements in various positions.

FIG. 8. shows a radio frequency probe connected to a coaxial cable 802 with integrated other types of sensors 812, 804, 808, 810 which may or may not be positioned as shown on or inside outer sleeve 814 or inner conductor 816. Integrated other types of sensors 812, 804, 808, 810 may be any type of one or more sensor, such as pressure sensor, temperature sensor, optical sensor, gas composition sensor, membrane or diaphragm sensor, thin film sensor, resistive or capacitive sensor, or other type of sensing device.

Figure 9:
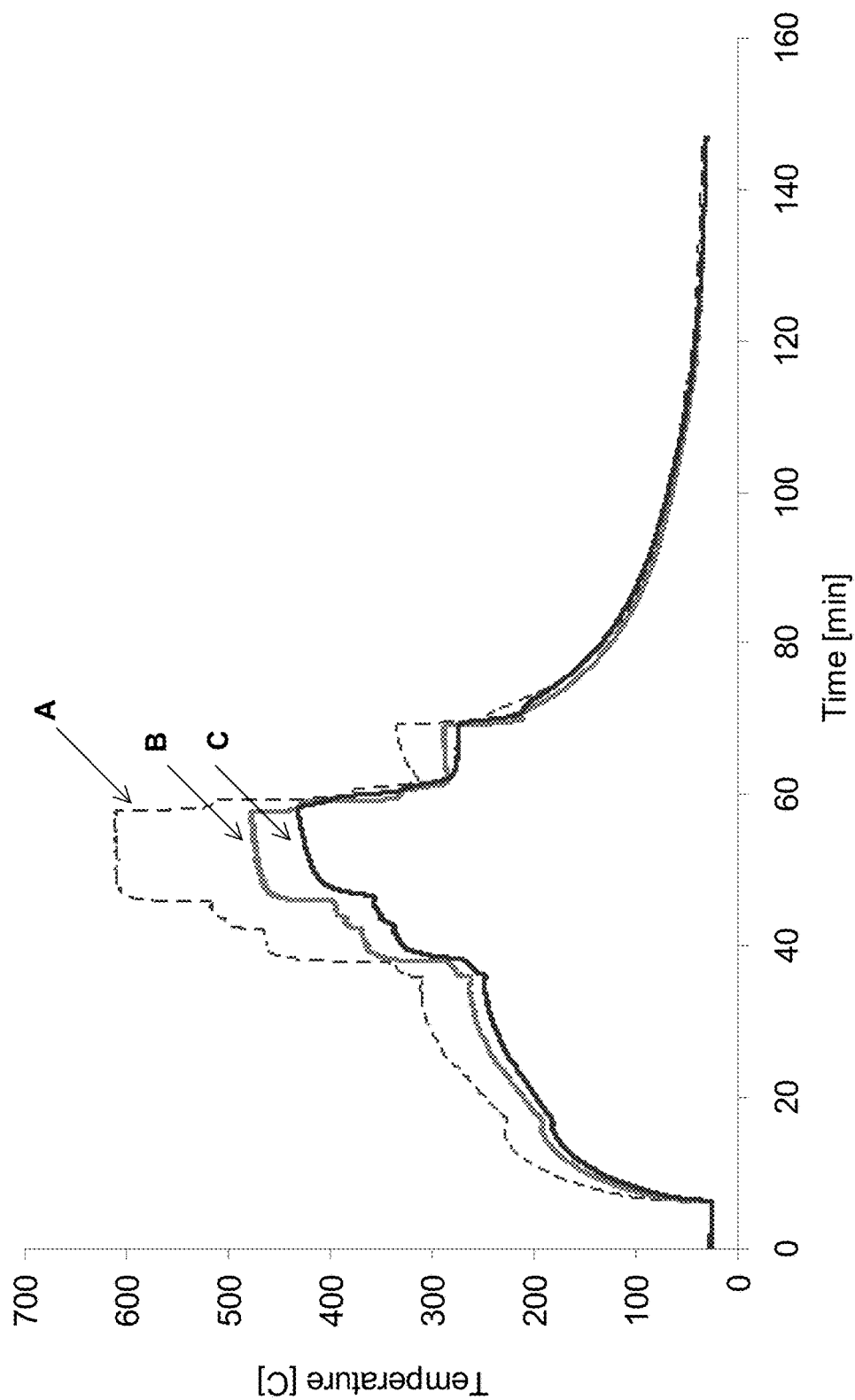
FIG. 9 is a plot of temperature measurements for two radio frequency probes with integrated temperature sensors compared with a conventional thermocouple, installed on a diesel burner system.

The performance of two radio frequency probes with integrated temperature sensor is shown in FIG. 9. The data in the figure was collected with two radio frequency probes containing integrated temperature sensors mounted in the inner conductor installed on opposite sides of a diesel particulate filter. The particulate filter was installed in the exhaust system of a diesel burner. For comparison, a thermocouple was also installed in the exhaust pipe upstream of the particulate filter. Temperature curve A in FIG. 9 corresponds to the measured exhaust temperature in the exhaust pipe upstream from the particulate filter. Temperature curves B and C correspond to the temperature measurements from the radio frequency probes with integral temperature sensors mounted near the inlet and outlet of the filter, respectively. In both cases the temperature response of the radio frequency probes with integral temperature sensors tracks very well with changes in the exhaust gas temperature upstream of the filter system measured by the thermocouple at point A. Temperatures B and C are, however, lower than A, due to heat losses from the exhaust system between point A and the particulate filter.

Figure 10:
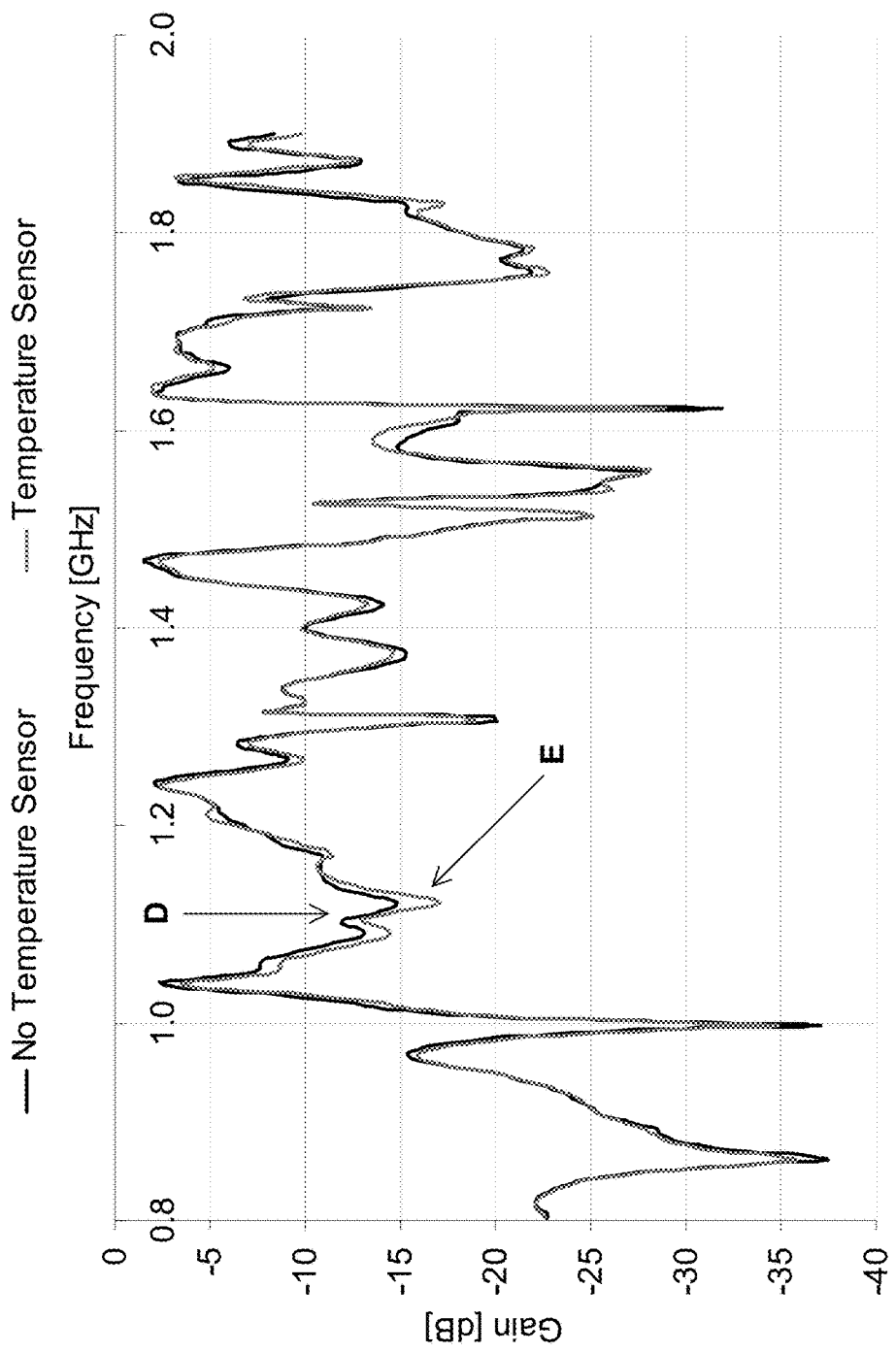
FIG. 10 are two radio frequency resonance curves for two probes, one with and one without an integrated temperature sensor showing less than 0.35% variation between the two signals.

FIG. 10 presents a comparison of the radio frequency transmission signal (S12) resonance curves corresponding to two identical antenna probes, one without a temperature sensor D and the other with an integrated temperature sensor E. There is no significant difference in the radio frequency performance of the probes D and E (less than 0.35% averaged over the resonance curve) due to the addition of the integrated temperature sensor. Similar measurements may also be conducted in reflection (S11 or S22).

Figure 11:
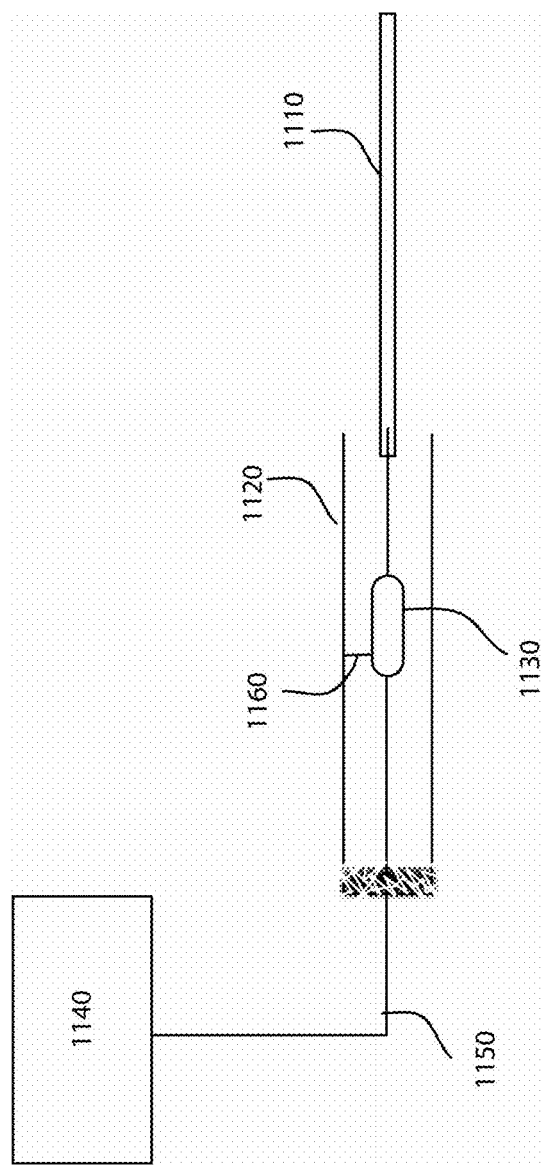
FIG. 11 shows an antenna integrated with a RF generator or a detector.

In order to minimize variability from antenna and to to provide simplicity, some of the RF electronics can be incorporated on the antenna. FIG. 11 shows a schematic of an antenna where the VCO or the source of the RF signal or the detector is placed inside the antenna body, thus eliminating any connections between the RF electronics and the antenna after fabrication. In FIG. 11, one end of the antenna 1110, and the ground electrode 1120 of the antenna are shown. The RF element (source or detector) 1130 is grounded to the ground electrode 1120 through connector 1160, and is connected to an outside electronic box 1140 via conduit 1150 that provides power and control to the RF element 1130. The RF element 1130 is connected internally to both the antenna 1110 and a ground electrode 1120 (although in principle, both electrodes are acting as antennas). Although FIG. 11 shows the source of the RF, it could instead be the detector of the RF or a combined transmitter and detector. The antenna assembly can be long enough in order to locate the RF electronics away from environments that can damage the electronics (such as temperature).

FIG. 12A shows a schematic where the antenna and the signal generator and additional RF electronics that are located inside the antenna assembly are surface mounted. The advantage of surface mounting the antenna and the other elements is both reduced cost of manufacturing as well as providing very reproducible antennas. Multiple antennas 1210 and 1220 can be placed in the unit 1260, if desired. For example, the antennas 1210, 1220 can be made using stripline techniques, or on a PC board 1240, or alternative surfaces that can be produced using microfabrication techniques. Complex antennae 1210 can be used, if desired, with tight tolerances. The RF electronics 1230 can be mounted on the PC board 1240 such that they are removed from environments that can be damaging to the electronics, such as temperature.

FIG. 12A shows a schematic where two antennae 1210 and 1220 are placed in the same unit (thus able to measure both S11 and S21 signals using a single unit 1260). One can be the transmitting antenna while the second one could be the receiving antenna. Alternatively, they can be both transmitting (or receiving) antennae with different phases, for adjusting the characteristics of the launched (received) wave. The number of parts can be decreased while maintaining the flexibility of measuring both transmission and reflection. The RF electronics 1230 both has the capability for generating the RF as well as the sensing capability for detecting the reflected signal to the transmitting antenna or the transmitted signal to the second antenna. The outside electronic box unit 1285 is placed outside of the unit 1260, and connected to the RF electronics 1230 through connector 1270.

In order to provide protection, the antenna assembly can be surrounded by a sheath made from a dielectric material (such as a ceramic, alumina for high temperature applications or an organic material for low temperature applications) which can be an integral part of the antenna or it could be an external unit. If external, it could be straight-forward to replace the antenna elements and the RF electronics without exchanging the dielectric sheath. The power and control unit of the RF element can be located outside of the antenna assembly.

An alternative assembly is shown in FIG. 12B. Instead of a second antenna, there is a hollow conducting tube 1280 that serves as the second electrode. A number of arrangements exist that can provide advantages, such as replacing the antenna element 1210 by a second hollow tube. The RF electronics 1230 is grounded to the antenna ground through element 1290 (not shown in FIG. 12A).

One advantage of the embodiments described in FIGS. 11-12 is the elimination of coaxial elements outside of the antenna, reducing costs and increasing reliability.

In addition to including the RF electronics onto the antenna, it is possible to include communication between the assembly and an external unit using wireless communication techniques. In this manner, the antenna is self-sufficient, without the needs of electrical connections to the external world. In this case, the antenna assembly needs to include a power source, which could be a battery. Some processing would be required to manage the data, using a processor on the antenna assembly.

The descriptions in FIGS. 11 and 12 are compatible with integrating other sensors onto the antenna assembly. Although dipole-like antennae are described, it would be possible to replace them with a loop or a series of loops. Also it would be possible to have multiple conducting elements in order to make phase-array antennae. In addition, the antennae may be a dielectric antennae, with dielectric elements for adjusting the frequency of operation, directionality of the emitted/received RF energy. Dielectric antennae are attractive because they could be used in environments where conventional conductive antennae could be not appropriate (because of electrical hazard, temperature or corrosive environment, for example). Dielectric antennae could be fed from a microstrip line and manufactured with surface mounted electrical and dielectric elements.

Figure 13:
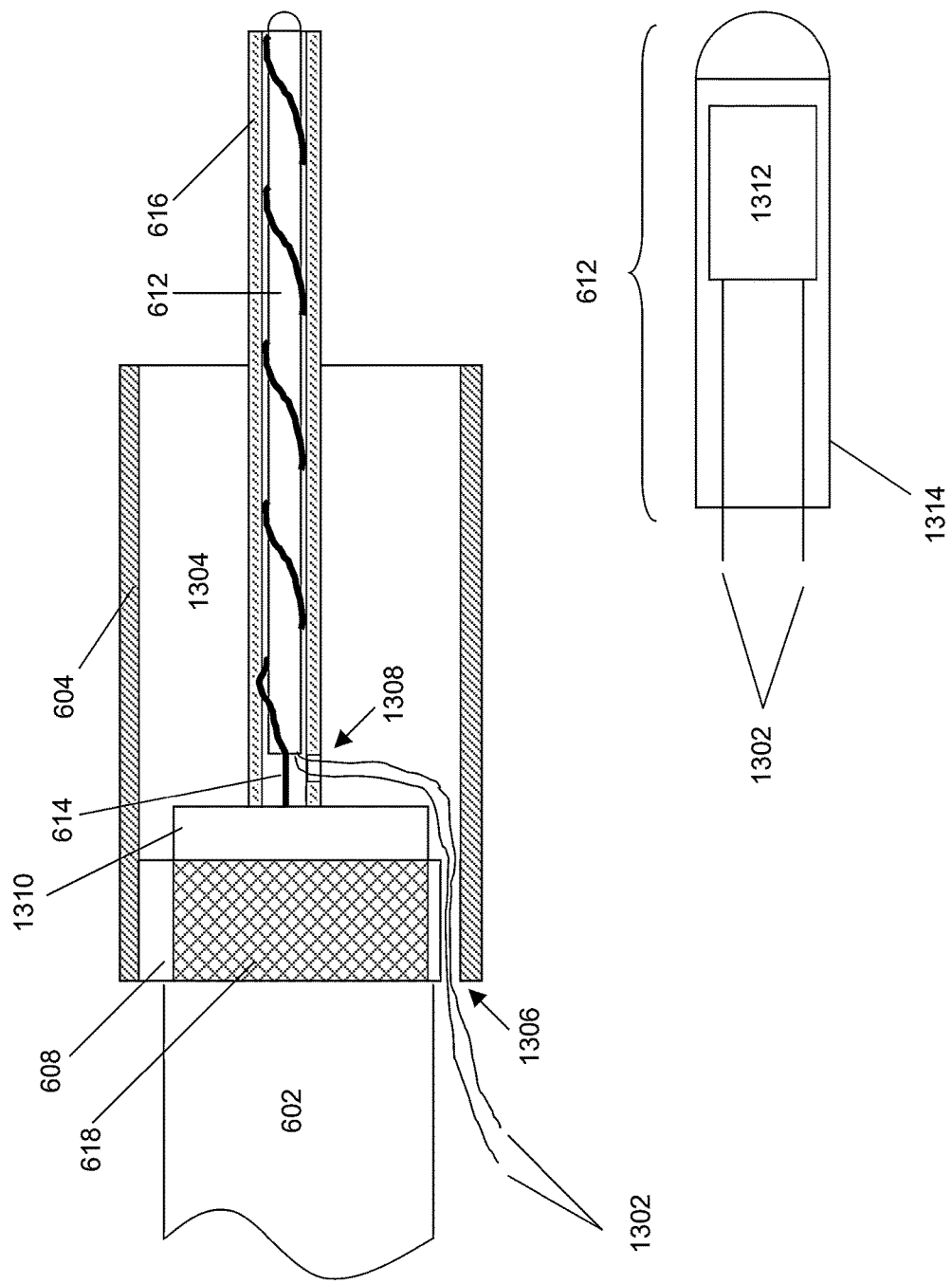
FIG. 13 is a cross-sectional view of an antenna probe integrated with a coaxial cable containing a second sensing element integrated into the antenna.

FIG. 13 depicts a further embodiment where an ancillary sensor 612 is integrated into a radio frequency measurement probe. A coaxial cable 602 may be attached to an outer sleeve 604 whereby coaxial braid 618 is in electrical contact with outer sleeve 604 through a crimp connection, solder connection, compression connection, or any other suitable means. Coaxial cable 602 need not be a coaxial cable, but may be any cable, such as twisted pair in one example, which may terminate with one conductor in electrical contact with outer sleeve 604 and a second conductor forming inner conductor 614.

Concentric spacer ring 608 may or may not be used. In the case where concentric spacer ring 608 is used, it may or may not contain a passage 1306 to enable wires or electrical conductors 1302 to pass through. Passage 1306 may contain an insulating material to insulate wires or conductors 1302 from each other and from outer sleeve 604 and from coaxial braid 618.

The radio frequency probe shown in FIG. 13 may contain an ancillary sensor 612, which may be in direct electrical contact with inner conductor 614. In one embodiment, inner conductor 614 may be wound around ancillary sensor 612. The number of windings of inner conductor 614 around ancillary sensor 612 may be used to control the degree or strength of electrical and mechanical coupling of the two components. In another embodiment, inner conductor 614 may not be wound around ancillary sensor 612 and may or may not be in electrical contact with ancillary sensor 612.

Inner conductor sheath 616 may or may not be used and may or may not extend the full length along ancillary sensor 612. In one embodiment, the region between inner conductor sheath 616, ancillary sensor 612 and inner conductor 614 may or may not be filled with some material, such as insulating or conductive material. In one embodiment, inner conductor 614 may be in electrical contact with inner conductor sheath 616 but may not be in electrical contact with ancillary sensor 612. In yet another embodiment, all three aforementioned elements may be in electrical contact. Inner conductor sheath 616 may or may not be conducting. In one embodiment, inner conductor sheath 616 may be metallic, such as stainless steel or Inconel. In another embodiment, inner conductor sheath 616 may be ceramic, glass, or plastic, or any other material.

When the ancillary sensor 612 is outside of a conducting inner conductor sheath, it is possible for the ancillary sensor 612 and conductors 1302 to act as an antenna extracting RF energy from the cavity and potentially irradiating outside of the system. It is desirable to prevent the RF energy from leaking from the system. It is possible to use capacitive elements, capacitive feedthroughs or magnetic elements (such as ferrites or other EMI cores) to prevent radiation from leaking through the passage 1306.

In one exemplary embodiment, ancillary sensor 612 may be a resistance temperature detector (RTD) or thermistor, but may be any sensor. Details of ancillary sensor 612 are shown in FIG. 13 and show one or more conductors 1302 extending from a casing 1314 containing a sensing element 1312. In one embodiment, sensing element 1312 may be a 200 Ohm platinum RTD, but may be any sensing element, including a thermocouple junction, piezo-electric element, strain gauge, or any other sensing element.

One or more conductors 1302 may be used to transmit the sensed signal or provide power or provide power and sense the signal from sensing element 1312. Any number of conductors 1302 may be used. Conductors 1302 may connect sensing element 1312 to signal conditioning circuits or measurement circuits, chips, or equipment, not shown. In the case of an RTD or thermocouple, conductors 1302 may be connected to an integrated circuit chip such as a thermocouple or RTD chip produced by Maxim, in one example, but any suitable chip or circuit may be used to process and interpret the sensed signal.

In the case where inner conductor sheath 616 is used, conductors 1302 may pass through the inner conductor sheath 616 and be electrically isolated from inner conductor sheath 616 by means of passage 1308. Conductors 1302 may or may not contain electrical insulation, such as a wire jacket or sleeve (not shown). The region 1304 within outer sleeve 604 may or may not be fully or partially filled with epoxy, sealant, potting compound, dielectric material, ceramic or glass discs, powders, high temperature matting material, or the like. In one exemplary embodiment, the back 30% abutting the coaxial cable 602 of the region 1304 may be filled with high temperature epoxy potting material sufficient to fully encapsulate conductors 1302 and fill passages 1308 and 1306 to provide electrical isolation, vibration damping, additional support and a sealed connection. The remaining 70% of the region 1304 may contain a high temperature matting material, however any proportion and any type of material may be used, depending on the application.

In another embodiment, inner conductor sheath 616 may extend over ancillary sensor 612 the same length as outer sleeve 604. Inner conductor 614 may only be wound around ancillary sensor 612 over the length covered by inner conductor sheath 616. In this embodiment, the full length of ancillary sensor 612 is exposed beyond outer sleeve 604 to provide improved measurement sensitivity or response time. Inner conductor 614 may be in direct electrical contact with ancillary sensor 612, thereby directly transmitting or receive the RF signal along the length of ancillary sensor 612.

The system disclosed in FIG. 13 has a number of advantages, specifically the high quality connection between inner conductor 614 and ancillary sensor 612 or inner conductor sheath 616. In addition, fully or partially filling region 1304 with matting material, potting compound, or the like provides a robust and durable assembly. Passages 1308 and 1306 enable electrical isolation of conductors 1302 from coaxial cable 602 and outer sleeve 604 and inner conductor sheath 616. Passages 1306 and 1308 may be a hole, slit, or any suitable passage. Any number of conductors 1302 may be used, such as in a two-, three- or four-wire RTD, or any other type of sensor.

Outer sleeve 604 may further be in contact with conducting cavity walls, such as a filter or catalyst housing, or conduit, but may be in contact with any walls or surface. In another example, outer sleeve 604 may not be in contact with any surface. Inner conductor sheath 616 may or may not be sealed or terminated at the end and ancillary sensor 612 may or may not protrude from inner conductor sheath 616. Inner conductor sheath 616 may or may not be connected to ancillary sensor 612 and inner conductor 614 by crimping, friction fit, solder, glue, or any other suitable means.

The operation of the radio frequency probe with integrated one or more ancillary sensors will now be described with reference to FIG. 1. In one method of operation, radio frequency control unit 102 generates and sends a radio frequency signal at a single frequency or multiple frequencies to one or more radio frequency probes 106. One or more radio frequency probes 106 may receive one or more radio frequency signals at one or more frequencies and transmit the received signal back to radio frequency control unit 102 by means of cable 110. The signal may be transmitted or received in a microwave resonant cavity 108 or in free space.

Radio frequency control unit 102 may also contain integrated sensing and processing electronics to monitor the signal received from one or more ancillary sensors integrated into radio frequency probes 106. In one example, the ancillary sensor 514 is a temperature sensor, which transmits a signal proportional to the sensed temperature to radio frequency control unit 102 via cables 110, but any sensed parameter may be monitored and transmitted. Cables 110 may be a multi-conductor cable assembly or wiring harness.

In another embodiment, radio frequency control unit 102 processes measurements or signals received from the radio frequency probes (radio frequency signals) along with one or more ancillary sensed values. Radio frequency signals may be corrected or modified by radio frequency control unit 102 based on or more ancillary sensed valued from radio frequency probe 106, such as multiplying or dividing the radio frequency signal by a correction factor. Any type of signal modification may be applied.

In one embodiment, one or more radio frequency signal parameters may be computed from the group consisting of quality factor, amplitude, frequency, frequency shift, phase, or some derivative of one or more of the aforementioned parameters. The radio frequency signal may or may not be at resonance. If at resonance, one or more resonant mode may be monitored. Additional statistics for the parameters may also be computed such as the mean, median, mode, standard deviation, or any other parameter.

Radio frequency control unit 102 may modify one or more of the radio frequency parameters or statistics based on one or more ancillary sensor values, such as temperature, pressure, flow, moisture measurements, gas composition measurements, or the like. The modification to the RF signal or calculated parameter may be via a single or multi-variable equation, transfer function, scaling factor, look-up table or the like. The modifications may be carried out by instructions, algorithms, or the like contained on a computer readable storage medium contained in radio frequency control unit 102 and executed by a processor disposed within the radio frequency control unit 102. The output of the raw or corrected radio frequency and ancillary sensed signals may be transmitted or communicated to process control unit 104 over a cable or wireless communication technique. Process control unit 104 may or may not be used and may or may not be separate but may be integrated into radio frequency control unit 102 or vice versa.

In one exemplary embodiment, the computed RF signal parameter is modified by means of a multi-variable equation which includes at least one additional variable determined from ancillary sensor measurements integrated into radio frequency probe 106 in order to compute a final value of the form:

$$\text{Final Value} = f(\text{RF\_Parameter}, \text{Ancillary\_Sensor\_Value}),$$

where the final value is a function of both the RF_parameter obtained from the RF probe and the value returned by the ancillary sensor.

In one particular embodiment, the equation may be:

$$\text{Final Value} = (\text{RF\_Parameter})(A) + (\text{Ancillary\_Sensor\_Value})(B)$$

However any number of additional ancillary sensor values or measurements and RF parameters may be used, and the equation may be first order or higher order or any form (exponential, logarithmic, trigonometric). The variables A and B may be constants, or derived from a look-up table or other means. In another example, any number of constants or other variables may be used. In one example, the final value is the soot or ash level on a particulate filter or the quantity of a gas phase component adsorbed on a catalyst, but may be any final value. In another embodiment, the ancillary sensor value may be derived from a sensor not integrated into the radio frequency probe 106, but in a preferred embodiment at least one ancillary sensor measurement is received from at least one ancillary sensor integrated into radio frequency probe 106.

The final value determined by the radio frequency control unit 102 may be stored in radio frequency control unit 102 or used to initiate an action, such as to stop or start a process, trigger an alarm, or some other action.

In another method of operation, radio frequency control unit 102 conducts a plausibility, or on-board diagnostic, check of radio frequency probe containing integrated at least one ancillary sensor 612 (see FIG. 6) to determine if the radio frequency transmission or reception is functioning correctly or whether or not the ancillary sensor is functioning correctly. In one example, the plausibility check or self diagnostic determines whether the sensor or antenna has failed. The plausibility check may be carried out at a known steady state condition (reference condition) or by monitoring the transient response or change in the signal's behavior. In the case of the RF transmission or detection function, the plausibility check may determine whether the signal strength or amplitude, power, frequency, phase or some derivative thereof is outside and acceptable limit value. The same method may be applied to the ancillary second sensor value, which me be compared with a known reference condition or an external sensor not integrated into radio frequency probe 106.

In one example, such as in the case of ancillary temperature sensor integrated into radio frequency probe 106, the plausibility check may include measuring resistance through the sensor, comparing sensor measurements to a reference state, such as plausible ambient conditions, or monitoring the transient response of the sensor to some perturbation or comparing the temperature values to a values from a known second or third sensor. Any other measurement parameter or ancillary sensor may be diagnosed by radio frequency control unit 102 in this manner.

The benefits of the system and method disclosed herein include highly robust and repeatable RF measurements from a probe capable of conducting one or more additional ancillary measurements from the same probe assembly. Another advantage includes the correction or modification of the RF signal based upon measurements of one or more ancillary sensors integrated into the same probe, as well as probe self diagnostics.

Although many of the examples cited in this disclosure relate to particulate filters, catalyst systems, and other emission control devices, the present apparatus may be applied to any type of system where radio frequency probes may be used, in any number of applications. Further, although the probes were described with reference to coaxial type cables, other types of cables, such as twisted pair may also be used.

While the above description contains much specificity, this should not be construed as limiting the scope of any embodiment, but as exemplifications of the presently preferred embodiments thereof. Many other ramifications and variations are possible within the teachings of the various embodiments.

Thus the scope of the invention should be determined by the appended claims and their legal equivalents, and not by the examples given.

What is claimed is:

1. A radio frequency probe system, comprising:
   a coaxial cable having an inner conductor directly surrounded by an inner dielectric material, the inner dielectric material covered by a conducting coaxial braid, and the conducting coaxial braid covered by an outer insulating jacket;
   a conductive outer sleeve in direct electrical contact with the coaxial braid; and
   an inner conductor sheath encasing the inner conductor, extending beyond the conducting outer sleeve.

2. The system of claim 1, further comprising a conductive inner sleeve disposed between the inner dielectric material and the conductive coaxial braid.

3. A radio frequency probe system, comprising:
   a coaxial cable having an inner conductor surrounded by an inner dielectric material, the inner dielectric material covered by a conducting coaxial braid, and the conducting coaxial braid covered by an outer insulating jacket;
   a conductive outer sleeve in direct electrical contact with the coaxial braid; and
   an inner conductor sheath encasing the inner conductor, extending beyond the conducting outer sleeve; and
   one or more crimp connections unitary with the conductive outer sleeve and positioned over and in direct contact with the conductive coaxial braid, whereby the conductive outer sleeve is mechanically compressed to contact the coaxial braid.

4. The system of claim 1, wherein the inner conductor extends further than the inner dielectric material, the coaxial braid and the outer insulating jacket.

5. The system of claim 1, wherein the inner conductor sheath comprises a conductive material.

\* \* \* \* \*